(12) United States Patent
Johal et al.

(10) Patent No.: US 7,276,584 B1
(45) Date of Patent: Oct. 2, 2007

(54) **ISOLATED NUCLEIC ACID MOLECULES ENCODING THE *BR2* P-GLYCOPROTEIN OF MAIZE AND METHODS OF MODIFYING GROWTH IN PLANTS TRANSFORMED THEREWITH**

(75) Inventors: Gurmukh S. Johal, West Lafayette, IN (US); Dilbag S. Multani, Urbandale, IA (US); Steven P. Briggs, Del Mar, CA (US)

(73) Assignees: Pioneer Hi-Bred International, Inc.; The Curators of the University of Missouri

( * ) Notice: Subject to any disclaimer, the term of this patent is extended or adjusted under 35 U.S.C. 154(b) by 0 days.

(21) Appl. No.: 11/338,199

(22) Filed: Jan. 24, 2006

Related U.S. Application Data

(60) Division of application No. 10/101,388, filed on Mar. 19, 2002, now Pat. No. 7,041,874, which is a continuation of application No. 09/711,562, filed on Nov. 13, 2000, now abandoned.

(60) Provisional application No. 60/164,886, filed on Nov. 12, 1999.

(51) Int. Cl.
*C07K 1/00* (2006.01)
(52) U.S. Cl. .................................... 530/350
(58) Field of Classification Search ............... 530/350
See application file for complete search history.

(56) References Cited

U.S. PATENT DOCUMENTS

| 6,750,380 B1 | 6/2004 | Johal et al. | |
| 7,041,874 B2 * | 5/2006 | Johal et al. | 800/290 |
| 2002/0162142 A1 * | 10/2002 | Johal et al. | 800/290 |

FOREIGN PATENT DOCUMENTS

WO    WO 01/34819 A2 * 5/2001

OTHER PUBLICATIONS

Bennetzen, J., et al., "Molecular Cloning of Maize Genes by Transposon Tagging with *Mutator*" *Plant Gene Systems and Their Biology*, 1987, pp. 183-204, Alan R. Liss, Inc.
Castiglioni, V., "Effects of the Introduction of the Brachytic-2-gene-br-2 in Seven Varies of Corn *Zea-mays* L," *Revista Ceres*, 1991, pp. 81-93, vol. 38(216).
Doerks, T., et al., "Protein Annotation: Detective Work for Function Prediction," 1998, *TIG* , pp. 248-250, vol. 14(6).
Dudler, R. and C. Hertig, et al., "Structure of an MDR-Like Gene from Arabidopsis-Thaliana Evolutionary Implications," *Journal of Biological Chemistry*, 1992, pp. 5882-5888, vol. 267(9).
Multani, D.S. et al., "Loss of an MDR Transporter in Compact Stalks of Maize *br2* and Sorghum *dw3* Mutants," *Science*, 2003, pp. 81-84, vol. 302.
Sandler, S.J. et al., "Inhibition of Gene Expression in Transformed Plants by Antisense RNA," *Plant Molecular Biology*, 1998, pp. 301-310, vol. 11(3), Kluwer Academic Publishers, Dordrecht, Netherlands.
Sidler, M., *et al.*, "Involvement of an ABC Transporter in a Developmental Pathway Regulating Hypocotyl Cell Elongation in the Light," *The Plant Cell*, 1998, pp. 1623-1636, vol. 10, American Society of Plant Physiologists.
Smart, C.C. and A.J. Fleming, "Hormonal and Environmental Regulation of a Plant PDR5-Like ABC Transporter," *The Journal of Biological Chemistry*, Aug. 1996, pp. 19351-19357, vol. 271(32), The American Society for Biochemistry and Molecular Biology, Inc., USA.
Spray, C., et al., "Cloning a Maize Dwarfing Gene by Transposon Tagging," *Plant Physiology*, 1995, p. 132, vol. 108(2) Supp., Annual Meeting of the American Society Plant Physiologists, USA.
Theodoulou, F.L., "Plant ABC Transports," *Biochimica et Biophysica Acta*, 2000, pp. 79-103, vol. 1465, Elsevier Science B.V.
Van Der Krol, A.R. et al., "Inhibition of Flower Pigmentation by Antisense CHS Genes: Promoter and Minimal Sequence Requirements for the Antisense Effect," *Plant Molecular Biology*, 1990, pp. 457-466, vol. 14(4), Kluwer Academic Publishers, Belgium.
Wang, W., et al., "A Potato cDNA Encoding a Homologue of Mammalian Multidrug Resistant P-Glycoprotein," *Plant Molecular Biology*, 1996, pp. 683-687, vol. 31(3).
Winkler, R., et al., "The Maize *Dwarf3* Gene Encodes a Cytochrome P450-Mediated Early Step in Gibberellin Biosynthesis," *The Plant Cell*, 1995, pp. 1307-1317, vol. 7, American Society of Plant Physiologists.

* cited by examiner

*Primary Examiner*—Karen Cochrane Carlson
*Assistant Examiner*—Agnes B. Rooke
(74) *Attorney, Agent, or Firm*—Alston & Bird LLP

(57) ABSTRACT

The invention relates to the genetic modification of plants, particularly to the expression of P-glycoprotein genes in transformed plants. Nucleotide sequences for the Br2 gene encoding a P-glycoprotein of maize and methods for their use are provided. The sequences find use in modifying the growth of plants.

6 Claims, 1 Drawing Sheet

ISOLATED NUCLEIC ACID MOLECULES ENCODING THE *BR2* P-GLYCOPROTEIN OF MAIZE AND METHODS OF MODIFYING GROWTH IN PLANTS TRANSFORMED THEREWITH

CROSS-REFERENCE TO RELATED APPLICATIONS

This application is a divisional of U.S. Utility application Ser. No. 10/101,388, filed Mar. 19, 2002 now U.S. Pat. No. 7,041,874, which is a continuation of U.S. Utility application Ser. No. 09/711,562, filed Nov. 13, 2000, now abandoned, which claims the benefit of U.S. Provisional Application No. 60/164,886, filed Nov. 12, 1999; all of which are hereby incorporated herein in their entirety by reference.

FIELD OF THE INVENTION

The present invention relates to the genetic manipulation of organisms, particularly plants, with genes that control growth and development. The invention further relates to genes that control growth, including homologues and mutant forms, the proteins encoded therefrom and plants transformed with these genes.

BACKGROUND OF THE INVENTION

Dwarf plants have had a major impact on agriculture. Dwarf varieties of wheat are widely used in North America due to both reduced potential for lodging and high yields. Dwarf fruit trees are also extensively used and allow farmers to produce more fruit per acre thereby increasing economic yield potential. There are other benefits that may be realized from the use of dwarf crop plants and dwarf fruit trees including reductions in the amounts of pesticides and fertilizers required, higher planting densities and reduced labor costs.

In view of the current trends of both increasing human population and the decreasing land area suitable for agriculture, increasing agricultural productivity is, and will continue to be, a challenge of paramount importance. Dwarf crop plants and fruit trees have been and will continue to be important components of our agricultural production system. Increased usage of dwarf crop plants and dwarf fruit trees may help to meet the agricultural production demands of the future. However, commercially acceptable dwarf varieties are not available for all crops.

In addition to the use of dwarf plants to control plant height, synthetic chemicals are routinely applied to certain economically important plant species to reduce growth. Plant growth regulators known as growth retardants are used to reduce stem elongation in a variety of crops including cotton, grape vines, fruit trees, peanuts, wheat and ornamentals such as azaleas, chrysanthemums, hydrangeas, poinsettias and many bedding plants. All of the commonly used growth retardants are inhibitors of gibberellin biosynthesis and limit stem or shoot growth by reducing elongation. In the United States, the most widely used growth retardant is mepiquat chloride, which is registered for use on cotton. Benefits attributed to the use of mepiquat chloride on cotton include increased yield, improved defoliation, improved stress tolerance, more uniform crop maturity and the ability to harvest earlier. Previously, the growth retardant daminozide was registered for use in the United States on apples, grapes and peanuts under the trademarks ALAR and KYLAR but was removed from use on food crops due to human health concerns. Despite the demands of agricultural producers for a product to replace diaminozide, there are no growth retardants registered for use on grapes, fruit trees and peanuts in the United States. Daminozide, however, is still widely used on certain non-food, plant species.

Uncovering the molecular mechanisms that control plant growth processes such as cell division and cell elongation will likely aid in the development of new plant varieties with reduced stature and new methods for reducing plant growth. Such new plant varieties and methods may provide both farmers and horticulturists with environmentally benign alternatives to the use of synthetic growth-retarding chemicals. Elongation of plant cells and organs is one of the most critical parameters of plant growth and development. Regulation of this trait in plants, however, is a fairly complicated process, as both external and internal factors influence it. The most important external stimulus is light, with its normally repressible or negative effect on cell elongation (Quail, P. H. (1995) *Science* 268:675-680; Kende et al. (1997) *Plant Cell* 9:1197-1210). The internal control of cell elongation is mediated by a number of chemicals, normally referred to as plant growth regulators or hormones (Kende et al. (1997) *Plant Cell* 9:1197-1210). Among the classical plant hormones, auxins and gibberellins (GAs) both promote cell elongation whereas cytokinins and abscisic acid each have been shown to have a negative effect on cell elongation (Kende et al. (1997) *Plant Cell* 9:1197-1210). Recently, another class of plant growth regulators, named brassinosteroids, has been identified that also dramatically promote plant growth (Yokota, T. (1997) *Trends Plant Sci.* 2:137-143; Azpiroz et al. (1998) *Plant Cell* 10:219-230; Choe et al. (1998) *Plant Cell* 10:231-243). However, the mechanisms by which plant hormones act, either singly or in concert, to control cell elongation remains unclear.

One way to gain an understanding of mechanisms that mediate cell elongation is to study mutants in which this aspect of plant growth is compromised (Klee et al. (1991) *Annu. Rev. Plant Physiol. Plant Mol. Biol.* 42:529-551). Numerous such mutants have been identified across most plant species, including maize, in which more than 25 single-gene mutations that affect plant stature have been characterized (Coe et al. (1988) In: *Corn & Corn Improvement*, G. F. Sprague (Ed.) Madison, Wis.; Sheridan, W. F. (1988) *Annu. Rev. Genet.* 22:353-385). These dwarf mutants are considered to be GA related, mainly because GA is the only phytohormone whose role in regulating height in maize has been convincingly established (Phinney et al. (1985) *Curr. Top. Plant Biochem. Physiol.* 4:67-74; Fujioka et al. (1988) *Proc. Natl. Acad. Sci. USA* 85:9031-9035). Both types of mutants, GA responsive and GA non-responsive, have been found in this collection of maize mutants. While genes for a number of GA-responsive mutants have been cloned and found to be involved in GA biosynthesis (Bensen et al. (1995) *Plant Cell* 7:75-84; Winkler et al. (1995) *Plant Cell* 7:1307-1317), nothing is known about the nature of defects in GA non-responsive maize mutants.

One type of GA non-responsive dwarf mutants that have received much attention from maize geneticists and breeders is called brachytic. These dwarfs are characterized by internodes of substantially reduced length, relative to wild type, without having any effect on the size or number of other organs, including the leaves, ear and tassel (Kempton, J. H. (1920) *J. Hered.* 11: 111-115). There are three known brachytic mutations in maize, br1, br2 and br3, all of which are recessive (Coe et al. (1988) In: *Corn & Corn Improvement*, G. F. Sprague (Ed.) Madison, Wis.; Sheridan, W. F. (1988) *Annu. Rev. Genet.* 22:353-385). Because of the commercial interest in br2 for enhancing plant productivity (Pendleton et al. (1961) *Crop Sci.* 1:433-435; Duvick, D. N. (1977) *Maydica* 22:187-196; Djisbar et al. (1987) *Maydica* 32:107-123; Russel, W. A. (1991) *Adv. Agron.* 46:245-298), this dwarf has been characterized the most. Depending on the genetic background, plants homozygous recessive for br2 are 30-70% shorter than their normal sibs. This reduction in plant height is exclusively due to a reduction of the length of stalk (stem) internodes. In addition to being dwarf, br2 mutants grown under greenhouse conditions often suffer from buggy whip, a disease-like condition in which the unfurling leaves in the whorl undergo necrosis and stay stuck together. This condition often results in the death of the growing tip of the plant.

To keep up with the demand for increased agricultural production, new targets are needed for genetically engineering agricultural plants for the improvement of agronomic characteristics. Elucidating the molecular mechanisms of cell division and elongation will provide new targets for agricultural scientists to manipulate.

SUMMARY OF THE INVENTION

Compositions and methods for expressing genes encoding P-glycoproteins in plants are provided. The compositions comprise nucleotide sequences encoding P-glycoproteins, particularly P-glycoproteins that control plant growth. The compositions further comprise nucleotide sequences of the br2 gene of maize. The sequences of the invention are useful in transforming plants for tissue-preferred or constitutive expression of P-glycoproteins and for isolating homologous nucleotide molecules that encode P-glycoproteins. Such sequences find use in methods for controlling the growth of organisms, particularly stem growth in plants. The sequences of the invention also find use in methods of enhancing the resistance of plants to pathogens.

The invention further encompasses methods for isolating nucleotide molecules that are capable of controlling the growth of plants. Such methods find use in the isolation of genes involved in plant growth processes.

Methods are provided for identifying plants that possess a mutant allele that is capable of conferring a stable mutant phenotype on an organism. Such methods find use in agriculture, particularly in the breeding of dwarf crop plants. Additionally provided are stable dwarf plants and seeds thereof.

Expression cassettes comprising the sequences of the invention are provided. Additionally provided are transformed plants, plant tissues, plant cells and seeds thereof. Isolated proteins encoded by the nucleotide sequences of the invention are provided.

DETAILED DESCRIPTION OF THE INVENTION

Figure 1:
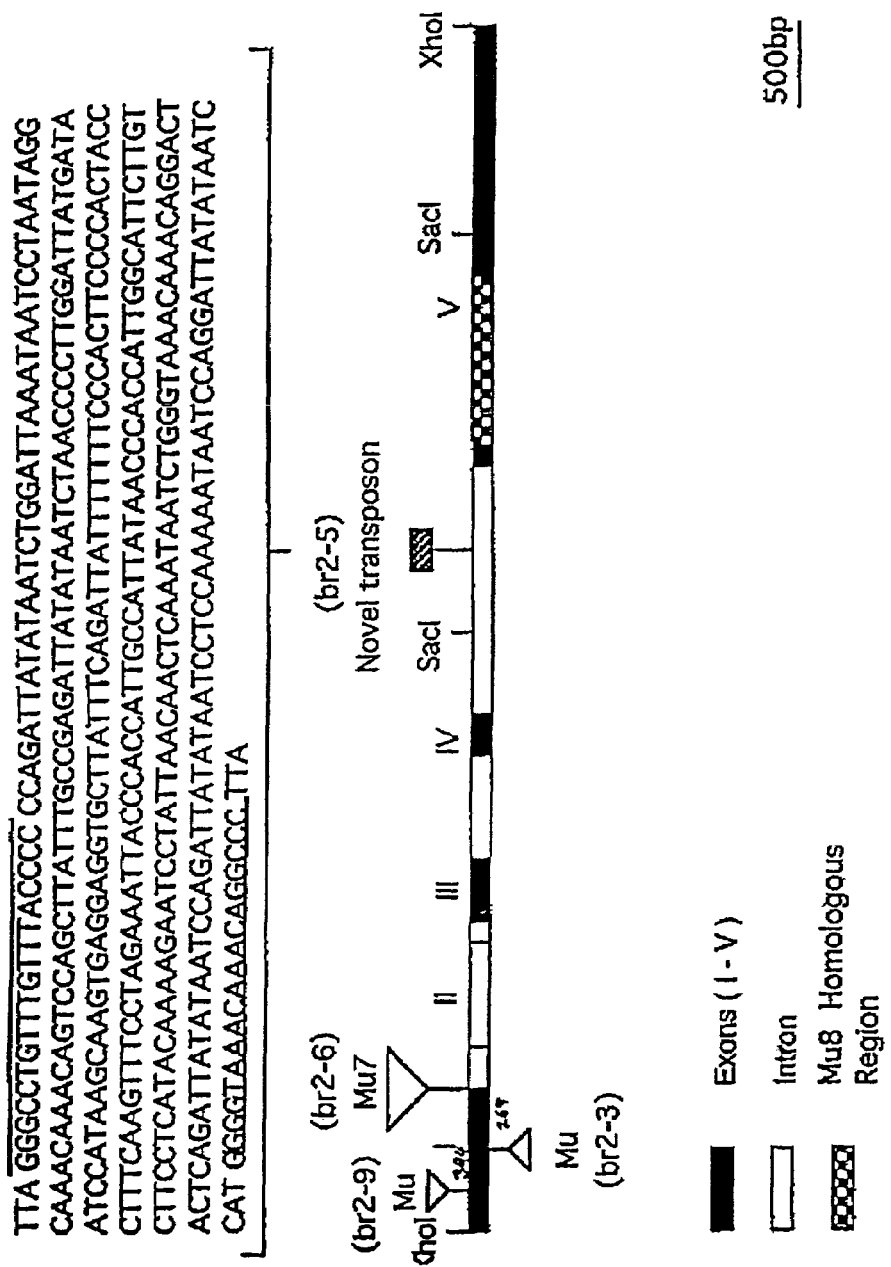
FIG. 1 schematically illustrates the 7.0 kb XhoI maize genomic clone containing most of the Br2 gene. Sites of Mu element insertions are indicated for the br2-3, br2-6 and br2-9 alleles as well as the novel transposon in br2-5.

The present invention is drawn to compositions and methods for controlling growth in organisms by transforming the organism with nucleotide sequences corresponding to P-glycoproteins, referred to as P-glycoprotein genes. In particular, the sequences are useful for controlling stem growth in plants. Thus, transformed plants, plant cells, plant tissues and seed are provided. Compositions are nucleic acids and proteins relating to P-glycoprotein or P-glycoprotein-like genes in plants. More particularly, nucleotide sequences for the br2 gene of maize and the amino acid sequence for the protein encoded thereby are disclosed. The sequences find use in the construction of expression vectors for subsequent transformation into plants of interest, as probes for the isolation of other P-glycoprotein-like genes, as molecular markers, and the like.

The present invention discloses the first unequivocal evidence of the involvement of multidrug-resistance-like-gene-encoded P-glycoproteins in the control of growth and development in an organism. Thus, it is recognized that any P-glycoprotein known in the art that affects growth and development can be used in the practice of the invention. For example, five other plant P-glycoproteins are known. See, for example Dudler et al. (1998) *Methods Enzym.* 292:162-173 (Arabidopsis), Davies et al. (1997) *Gene* 199:195-202 (Barley), Wang et al. (1996) *Plant Mol. Biol.* 31:683-687 (Potato) and GenBank Accession Numbers Y10227 and Y15990 (both from *Arabidopsis*); herein incorporated by reference. These and other P-glycoprotein sequences can be tested for an effect on growth by methods such as transformation with antisense sequences and monitoring effects on progeny plants.

Compositions of the invention include the native nucleotide sequences for P-glycoprotein genes, antisense sequences, as well as variants and fragments thereof. Particularly, the P-glycoprotein gene of the maize Br2 locus and the respective amino acid sequence for the P-glycoprotein encoded thereby, as well as fragments and variants thereof, are provided. The Br2 sequences are set forth in SEQ ID NOS: 1-3. The sequences or corresponding antisense sequences find use in modulating the expression of a P-glycoprotein in a plant or plant cell. That is, the coding sequences can be used to increase the expression while antisense sequences can be used to decrease expression.

The sequences of the invention find use in methods of modifying the growth of an organism. In one embodiment of the invention, nucleotide sequences of the invention find use in methods of modifying plant growth. Toward this end, the sequences of the invention may be utilized in expression cassettes or nucleotide constructs operably linked to any one of a variety of plant promoters. Aspects of plant growth that may be impacted by the methods of the invention include, but are not limited to, plant height; the size, shape and number of cells and organs; cell division rate; cell elongation rate; the growth rate of the plant, its organs, tissues and cells; timing and location of organ initiation; life span; and the like.

The invention discloses methods for reducing plant growth which find use as alternatives to applying synthetic, growth-retarding chemicals to plants. These methods provide environmentally safe alternatives to traditional means of retarding stem elongation or growth with synthetic chemicals. Certain embodiments of the invention make use of plants transformed with tissue-preferred promoters, particularly stem-preferred promoters, operably linked to nucleotide sequences encoding P-glycoproteins.

Methods of the invention include transformation of plants with nucleotide sequences of the invention to reduce plant growth. The nucleotide sequences may be used in either the sense or antisense orientation to suppress the level of an endogenous P-glycoprotein that controls the growth of a plant. By reducing the level in a plant of such a P-glycoprotein, particularly one that controls stem or stalk growth, a plant of reduced stature, a dwarf plant, can be produced.

Dwarf plants having improved agronomic characteristics, such as reduced potential for lodging, increased water-use efficiency, reduced life cycle, increased harvest efficiency and increased yield per unit area are obtained by these methods. The methods of the invention can eliminate the need to graft shoots of fruit trees on dwarfing rootstocks to produce dwarf fruit trees.

The methods of the invention find use in producing dwarf varieties of crop plants. In one embodiment of the invention, a dwarf Basmati rice plant is produced by transforming the plant with a nucleotide sequence encoding at least a portion of a P-glycoprotein that controls the growth of a plant. Basmati rice, known for its aromatic fragrance, slender, elongated grains, and relatively short cooking time, is the favorite type of rice of the majority of people in the Indian sub-continent. While commercially acceptable dwarf cultivars have been developed for other types of rice, previous attempts to produce commercially acceptable varieties of Basmati rice by traditional plant breeding methods have failed. While dwarf plants were obtained in such attempts, some of the distinctive grain characteristics that consumers expect in Basmati rice were not retained in the dwarf plants. The methods of the invention provide a means of making dwarf Basmati rice plants that produce grain possessing the characteristics desired by consumers.

The desired dwarf Basmati rice plants are produced by transforming a non-dwarf Basmati rice plant with a nucleotide sequence of the invention operably linked to a promoter that drives expression in a plant. While the choice of promoter depends on the desired outcome, the preferred promoters are tissue-preferred promoters, particularly stem-preferred promoters. Through cosuppression or antisense suppression, such plants produce reduced levels of at least one P-glycoprotein that controls growth of the rice plant, particularly stem growth. Preferably, the nucleotide sequence encodes at least a portion of a P-glycoprotein that controls the growth of a plant. More preferably, the nucleotide sequence is selected from the group consisting of SEQ ID NO: 1, SEQ ID NO: 2 or a nucleotide sequence that encodes the amino acid sequence set forth in SEQ ID NO: 3. Most preferably, the nucleotide sequence is from a rice gene that is homologous to Br2 from maize. Such a rice gene encodes a P-glycoprotein that controls stem growth of the rice plant. The methods of the invention comprise transforming plants with the full-length nucleotide sequences of the invention or any fragment or part thereof.

Methods for enhancing the resistance of plants to pathogens are provided. It is recognized that P-glycoproteins are involved in resistance mechanisms against pathogens. A mutant strain of the nematode, *Caenorhabditis elegans*, with deletions of two P-glycoprotein genes is substantially more susceptible to death than wild type nematodes when placed on a lawn of a *Pseudomonas aeruginosa* strain that is a pathogen of both plants and animals (Mahajan-Miklos et al. (1999) *Cell* 96:47-56). It is recognized that br2 maize plants, under certain cultural conditions, can display a phenotype know as "buggy whip" which mimics a bacterial pathogen-induced necrosis of the growing tip of a plant. Plants are transformed with the nucleotide sequences of the invention operably linked to promoters that drive expression in a plant. Such plants can display enhanced resistance to pathogens, including bacteria, fungi, viruses, nematodes and insects. The methods find use in agriculture for limiting the impact of plant pathogens on crop production and provide an alternative to the use of synthetic pesticides in controlling plant pathogens.

Methods are provided for isolating nucleotide molecules that are capable of controlling the growth of plants. Such methods involve the loss of function of a gene by the insertion of a transposon with a known sequence into the gene. The transposon can be naturally occurring in the genome of a plant, or introduced into the genome by artificial methods, such as, for example, transformation. The transposon-containing gene or nucleotide molecule can be isolated by making use of the known sequences of the transposon. Any one of a variety of techniques to isolate the transposon-containing gene that is known to those skilled in the art can be employed including, but not limited to, inverse PCR, genomic DNA cloning using the transposon as a hybridization probe, and the like. The methods involve crossing a wild-type plant with a plant having the desired mutant phenotype. At least one of the participants in such a cross must contain at least one transposon, and the combined genomes of the participating plants must contain all the genetic elements necessary for transposition including, but not limited to, a transposon or transposable element and a nucleotide sequence encoding a transposase. Such a transposase may, or may not, be encoded by a nucleotide sequence that is within the transposon. Preferably, the mutant phenotype can result from a single genetic locus in a homozygous recessive state. From the resulting $F_1$ progeny of the cross-pollination, an individual with the mutant phenotype is selected, its genomic DNA is isolated and the transposon-containing gene is isolated from the genomic DNA. It is recognized that the isolated transposon-containing gene or nucleotide molecule can comprise at least one transposon, or a portion thereof. Once the transposon-containing gene is isolated, it can be sequenced to determine the identity of the gene and used to isolate a wild-type form of the gene from a wild-type plant. In a method of the invention, the Br2 gene of maize is isolated.

The nucleotide sequences of the invention find use in methods for identifying nucleotide sequences encoding gene products that control plant growth. Such gene products, like the BR2 protein, impact or modify the growth of a plant in detectable way by, for example, affecting characteristics such as the height or shape of a cell, organ or the plant body itself, cell number, cell division rate or cell elongation rate, organ growth rate, appearance of reproductive structures, timing and location of organ initiation and the like. The methods of the invention are particularly directed toward nucleotide sequences which influence the height or stature of a plant. The nucleotide sequences of the invention find use in any method known to those skilled in the art for identifying homologous sequences. Such methods for identifying homologous sequences include PCR amplification, hybridization, Southern blotting, colony hybridization and the like.

In an embodiment of the invention, the nucleotide sequence is selected from the group consisting of the nucleotide sequences set forth in SEQ ID NO: 1 and SEQ ID NO: 2, and a nucleotide sequence encoding the amino acid sequence set forth in SEQ ID NO: 3. Such a nucleotide sequence is used to design at least one hybridization probe or PCR primer which is then used to identify a gene in the genome of a Basmati rice plant that is homologous to the maize gene Br2. Preferably, such a gene from a Basmati rice plant encodes P-glycoprotein. More preferably, such a gene encodes a P-glycoprotein that controls the growth of a Basmati rice plant. Most preferably, such a gene encodes a P-glycoprotein that controls the stem growth of a Basmati rice plant.

The P-glycoproteins of the invention encompass all polypeptides and nucleotide sequences encoding them that share substantial sequence identity to the sequences of the invention whether or not such polypeptides possess covalently attached carbohydrates or carbohydrate-containing chains.

By "control growth of an organism" is intended to include impacting, modifying, modulating, affecting, increasing, and decreasing growth and growth-related processes of an organism. Such processes may influence any of a multitude of characteristics of an organism including, but not limited to, cell size and shape, organism size and shape, cell division rate, cell enlargement rate, organ growth rate, onset of reproductive maturity and life span.

By "mutant phenotype" is intended any non-wild-type, non-typical or non-standard phenotype which occurs as a result of a genetic alteration in the genome of an organism. When used in reference to domesticated plants and animals, a "mutant phenotype" is any phenotype that is substantially different from the typical phenotype of the particular domesticated breed or cultivated variety from which the mutant phenotype arose.

By "mutant plant" is intended a plant having a mutant phenotype.

By "mutant allele" is intended an allele of a gene that is capable of causing a "mutant phenotype."

By "dwarf" is intended atypically small. By "dwarf plant" is intended an atypically small plant. Generally, such a "dwarf plant" has a stature or height that is reduced from that of a typical plant by about 5%, 10%, 15%, 20%, 25%, 30%, 35%, 40%, 45%, 50%, 55%, 60% or greater. Generally, but not exclusively, such a dwarf plant is characterized by a reduced stem, stalk or trunk length when compared to the typical plant.

By "nucleotide molecule" is intended a molecule composed of nucleotides covalently bound to one another. Nucleotides include both ribonucleotides and deoxyribonucleotides. "Nucleotide molecule" encompasses single-stranded and double stranded forms of both DNA and RNA. "Nucleotide molecules" may be naturally occurring, synthetic or a combination of both. The linear arrangement of nucleotides in a "nucleotide molecule" is referred to as a "nucleotide sequence" and unless specified otherwise is presented herein from left to right corresponding to 5'-to-3' direction. Because of the complementary nature of the opposite strands of a double-stranded nucleotide molecule, a nucleotide sequence of the invention additionally encompasses its complementary antisense sequence.

Compositions of the invention include native nucleotide sequences for genes encoding multidrug-resistance-like-gene-encoded P-glycoproteins, homologues of multidrug-resistance-like-gene-encoded P-glycoproteins, antisense sequences, as well as fragments and variants and fragments thereof. In particular, the present invention provides for isolated nucleic acid molecules comprising nucleotide sequences encoding the amino acid sequences set forth in SEQ ID NO: 3, or the nucleotide sequences encoding the DNA sequences deposited in a bacterial host as Patent Deposit No. PTA-2646. Further provided are polypeptides having an amino acid sequence encoded by a nucleic acid molecule described herein, for example those set forth in SEQ ID NOS: 1 and 2, those deposited in a bacterial host as Patent Deposit No. PTA-2646, and fragments and variants thereof.

Plasmids containing the nucleotide sequences of the invention were deposited with the Patent Depository of the American Type Culture Collection (ATCC), Manassas, Va., Nov. 1, 2000 and assigned Patent Deposit Nos. PTA-2646. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. §112.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain biological activity of the native P-glycoprotein and hence retain one or more functions of the native P-glycoprotein such as, for example, transmembrane transporter activity and ATP binding. Alternatively, fragments of a nucleotide sequence that are useful as hybridization probes may or may not encode protein fragments retaining biological activity. Thus, fragments of a nucleotide sequence may range from at least about 20 nucleotides, about 50 nucleotides, about 100 nucleotides, and up to the full-length nucleotide sequence of the invention.

A fragment of a P-glycoprotein gene nucleotide sequence that encodes a biologically active portion of a P-glycoprotein of the invention will encode at least 15, 25, 30, 50, 100, 150, 200, 250, 300, 350, 400, 450, 500, 550, 600, 650, 700, 800, 900, 1000, 1100, 1200 or 1300 contiguous amino acids, or up to the total number of amino acids present in a full-length P-glycoprotein of the invention (for example, 1394 amino acids for SEQ ID NO: 3). Fragments of a P-glycoprotein gene nucleotide sequence that are useful as hybridization probes for PCR primers generally need not encode a biologically active portion of a P-glycoprotein.

Thus, a fragment of a P-glycoprotein gene nucleotide sequence may encode a biologically active portion of a P-glycoprotein, or it may be a fragment that can be used as a hybridization probe or PCR primer using methods disclosed below. A biologically active portion of a P-glycoprotein can be prepared by isolating a portion of one of the P-glycoprotein gene nucleotide sequences of the invention, expressing the encoded portion of the P-glycoprotein e.g., by recombinant expression in vitro), and assessing the activity of the portion of the P-glycoprotein. Nucleic acid molecules that are fragments of a P-glycoprotein gene nucleotide sequence comprise at least 16, 20, 50, 75, 100, 150, 200, 300, 500, 700, 1,000, 1,500, 2,000, 3,000, 4,000, 5,000, 6,000 7,000 or 8,000 nucleotides, or up to the number of nucleotides present in a full-length P-glycoprotein nucleotide sequence disclosed herein (for example, 8,036 and 4,653 nucleotides for SEQ ID NOS: 1 and 2, respectively).

By "variants" is intended substantially similar sequences. For nucleotide sequences, conservative variants include those sequences that, because of the degeneracy of the genetic code, encode the amino acid sequence of one of the P-glycoprotein polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a P-glycoprotein protein of the invention. Generally, variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, transporter activity or ATP binding activity as described herein. Such variants may result from, for example, genetic polymorphism or from human manipulation. Biologically active variants of a native P-glycoprotein of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the P-glycoproteins can be prepared by mutations in the DNA. Methods for mutagenesis and nucleotide sequence alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired transporter activity. Obviously, the mutations that will be made in the DNA encoding the variant must not place the sequence out of reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays.

Variant nucleotide sequences and proteins also encompass nucleotide sequences and proteins derived from a mutagenic and recombinogenic procedure such as DNA shuffling. With such a procedure, one or more different P-glycoprotein coding sequences can be manipulated to create a variant nucleotide sequence encoding a variant P-glycoprotein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the P-glycoprotein gene of the invention and other known P-glycoprotein genes to obtain a new gene coding for a protein with an improved property of interest, such as an increased $\mu m$ in the case of an enzyme. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2nd ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the P-glycoprotein gene nucleotide sequences of the invention. Methods for preparation of probes for hybridization and for construction of cDNA and genomic libraries are generally known in the art and are disclosed in Sambrook et al. (1989) *Molecular Cloning: A Laboratory Manual* (2nd ed., Cold Spring Harbor Laboratory Press, Plainview, N.Y.).

For example, an entire Br2 sequence disclosed herein, or one or more portions thereof, may be used as a probe capable of specifically hybridizing to corresponding P-glycoprotein gene sequences and messenger RNAs. To achieve specific hybridization under a variety of conditions, such probes include sequences that are unique among P-glycoprotein gene sequences and are preferably at least about 10 nucleotides in length, and most preferably at least about 20 nucleotides in length. Such probes may be used to amplify corresponding P-glycoprotein gene sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2nd ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least two-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. The duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)–0.61 (% form)–500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10C lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2nd ed., Cold Spring Harbor Laboratory Press, Plainview, N.Y.).

Thus, isolated sequences that encode for P-glycoproteins and which hybridize under stringent conditions to the to the P-glycoprotein gene sequences disclosed herein, or to fragments thereof, are encompassed by the present invention. Such sequences will be at least about 70% to 75%, about 80% to 85%, and even 90%, 91%, 92%, 93%, 94%, 95%, 96%, 97%, 98%, 99% or more homologous with the disclosed sequences. That is, the sequence identity of sequences may range, sharing at least about 70% to 75%, about 80% to 85%, and even at least about 75%, 80%, 85%, 90%, 91%, 92%, 93%, 94%, 95%, 96%, 97%, 98%, 99% or more sequence identity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity". (a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988) *CABIOS* 4:11-17; the local homology algorithm of Smith et al. (1981) *Adv. Appl. Math.* 2:482; the homology alignment algorithm of Needleman and Wunsch (1970) *J. Mol. Biol.* 48:443-453; the search-for-similarity-method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) Gene 73:237-244 (1988); Higgins et al. (1989) CABIOS 5:151-153; Corpet et al. (1988) Nucleic Acids Res. 16:10881-90; Huang et al. (1992) CABIOS 8:155-65; and Pearson et al. (1994) Meth. Mol. Biol. 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) J. Mol. Biol. 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) Nucleic Acids Res. 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See http://www.ncbi.hlm.nih.gov. Alignment may also be performed manually by inspection. Unless otherwise stated, sequence identity/similarity values provided herein refer to the value obtained using GAP Version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

GAP uses the algorithm of Needleman and Wunsch (1970) J. Mol. Biol. 48: 443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) Proc. Natl. Acad. Sci. USA 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The use of the term "nucleotide constructs" herein is not intended to limit the present invention to nucleotide constructs comprising DNA. Those of ordinary skill in the art will recognize that nucleotide constructs, particularly polynucleotides and oligonucleotides, comprised of ribonucleotides and combinations of ribonucleotides and deoxyribonucleotides may also be employed in the methods disclosed herein. Thus, the nucleotide constructs of the present invention encompass all nucleotide constructs that can be employed in the methods of the present invention for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs of the invention also encompass all forms of nucleotide constructs including, but not limited to, single-stranded forms, double-stranded forms, hairpins, stem-and-loop structures, and the like.

Furthermore, it is recognized that the methods of the invention may employ a nucleotide construct that is capable of directing, in a transformed plant, the expression of at least one protein, or at least one RNA, such as, for example, an antisense RNA that is complementary to at least a portion of an mRNA. Typically such a nucleotide construct is comprised of a coding sequence for a protein or an RNA operably linked to 5' and 3' transcriptional regulatory regions. Alternatively, it is also recognized that the methods of the invention may employ a nucleotide construct that is not capable of directing, in a transformed plant, the expression of a protein or an RNA.

In addition, it is recognized that methods of the present invention do not depend on the incorporation into the genome of the entire nucleotide construct comprising a P-glycoprotein nucleotide sequence, only that the plant or cell thereof is altered as a result of the introduction of the nucleotide construct into a cell. In one embodiment of the invention, the genome may be altered following the introduction of the nucleotide construct into a cell. For example, the nucleotide construct, or any part thereof, may incorporate into the genome of the plant. Alterations to the genome of the present invention include, but are not limited to, additions, deletions, and substitutions of nucleotides in the genome. While the methods of the present invention do not depend on additions, deletions, or substitutions of any particular number of nucleotides, it is recognized that such additions, deletions, or substitutions comprise at least one nucleotide.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) *Proc. Natl. Acad. Sci. USA* 96:8774-8778; herein incorporated by reference.

The invention encompasses the use of methods, such as, for example, chimeraplasty to alter P-glycoprotein genes in plants. Such alterations include, for example, changes in the coding sequence that alter the amino acid sequence of the P-glycoprotein encoded thereby, resulting in a reduction in, or loss of, the function of the P-glycoprotein encoded by that gene.

The P-glycoprotein nucleotide sequences of the invention are provided in expression cassettes for expression in the plant of interest. The cassette will include 5' and 3' regulatory sequences operably linked to a P-glycoprotein nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the P-glycoprotein nucleotide sequence to be under the transcriptional regulation of the regulatory regions. The expression cassette may additionally contain selectable marker genes.

The expression cassette will include in the 5'-3' direction of transcription, a transcriptional and translational initiation region, a P-glycoprotein nucleotide sequence of the invention, and a transcriptional and translational termination region functional in plants. The transcriptional initiation region, the promoter, may be native or analogous or foreign or heterologous to the plant host. Additionally, the promoter may be the natural sequence or alternatively a synthetic sequence. By "foreign" is intended that the transcriptional initiation region is not found in the native plant into which the transcriptional initiation region is introduced.

While it may be preferable to express the sequences using heterologous promoters, the native promoter sequences may be used. Such constructs would change expression levels of a P-glycoprotein in the plant or plant cell. Thus, the phenotype of the plant or plant cell is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5'-leader sequences in the expression cassette construct. Such leader sequences can act to enhance translation. Translation leaders are known in the art and include: picornavirus leaders, for example, EMCV leader (Encephalomyocarditis 5'-noncoding region) (Elroy-Stein et al. (1989) *PNAS USA* 86:6126-6130); potyvirus leaders, for example, TEV leader (Tobacco Etch Virus) (Allison et al. (1986); MDMV leader (Maize Dwarf Mosaic Virus); *Virology* 154:9-20), and human immunoglobulin heavy-chain binding protein (BiP), (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

It is recognized that with the nucleotide sequences of the invention, antisense constructions, complementary to at least a portion of the messenger RNA (mRNA) for the P-glycoprotein gene sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, preferably 80%, more preferably 85% sequence identity to the corresponding target sequences may be used. Furthermore, portions of the antisense nucleotides may be used to disrupt the expression of the target gene. Generally, sequences of at least 50 nucleotides, 100 nucleotides, 200 nucleotides, or greater may be used.

The nucleotide sequences of the present invention may also be used in the sense orientation to suppress the expression of endogenous genes in plants. Methods for suppressing gene expression in plants using nucleotide sequences in the sense orientation, also known as cosuppression methods, are known in the art. The methods generally involve transforming plants with a nucleotide construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, preferably greater than about 65% sequence identity, more preferably greater than about 85% sequence identity, most preferably greater than about 95% sequence identity. See, U.S. Pat. Nos. 5,283,184 and 5,034,323; herein incorporated by reference.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). See generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. Aci. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillen and-Wissman (1989) *Topics Mol. Struc. Biol.* 10: 143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention. The promoters may be selected based on the desired timing, localization and level of expression of the P-glycoprotein genes in a plant. Constitutive, tissue-preferred, pathogen-inducible, wound-inducible and chemically regulatable promoters can be used in the practice of the invention.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Application Serial No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Tissue-preferred promoters can be utilized to target enhanced P-glycoprotein expression within a particular plant tissue. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2): 157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Leaf-preferred promoters include, Yamamoto et al. (1997) *Plant J.* 12(2):255-265; Kawamata et al. (1997) *Plant Cell Physiol.* 38(7):792-803; Hansen et al. (1997) *Mol. Gen. Genet.* 254(3):337-343; Russell et al. (1997) *Transgenic Res.* 6(2):157-168; Rinehart et al. (1996) *Plant Physiol.* 112(3): 1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol. Biol.* 23(6): 1129-1138; Matsuoka et al. (1993) *Proc. Natl. Acad. Sci. USA* 90(20):9586-9590; and Guevara-Garcia et al. (1993) *Plant J.* 4(3):495-505.

Root-preferred promoters are known and can be selected from the many available from the literature or isolated de novo from various compatible species. See, for example, Hire et al. (1992) *Plant Mol. Biol.* 20(2): 207-218 (soybean root-preferred glutamine synthetase gene); Keller and Baumgartner (1991) *Plant Cell* 3(10):1051-1061 (root-preferred control element in the GRP 1.8 gene of French bean); Sanger et al. (1990) *Plant Mol. Biol.* 14(3):433-443 (root-preferred promoter of the mannopine synthase (MAS) gene of *Agrobacterium tumefaciens*); and Miao et al. (1991) *Plant Cell* 3(1):11-22 (full-length cDNA clone encoding cytosolic glutamine synthetase (GS), which is expressed in roots and root nodules of soybean). See also Bogusz et al. (1990) *Plant Cell* 2(7):633-641, where two root-preferred promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-preferred promoter activity was preserved. Leach and Aoyagi (1991) describe their analysis of the promoters of the highly expressed rolC and rolD root-inducing genes of *Agrobacterium rhizogenes* (see *Plant*

Science (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root preferred in the intact plant and stimulated by wounding in leaf tissue, an especially desirable combination of characteristics for use with an insecticidal or larvicidal gene (see *EMBO J.* 8(2): 343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also the copending applications entitled "Inducible Maize Promoters", U.S. Application Ser. No. 60/076,100, filed Feb. 26, 1998, and U.S. Application Ser. No. 60/079,648, filed Mar. 27, 1998, both of which are herein incorporated by reference.

Of interest are promoters that are expressed locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path.* 41:189-200).

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J* 6(2):141-150); and the like, herein incorporated by reference.

Chemically regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717-2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923-926). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

Alternatively, the nucleotide sequences of the invention can be introduced into an organism and allowed to undergo recombination with homologous regions of the organism's genome. Such homologous recombination approaches are well known to those of ordinary skill in the art and can be used to stably incorporate sequences of the invention into an organism. Further, such strategies can be used to introduce "knockout mutations" into a specific gene of an organism that shares substantial homology to the sequences of the invention. A knockout mutation is any mutation in the sequence of a gene that eliminates or substantially reduces the function or the level of the product encoded by the gene. Methods involving transformation of an organism followed by homologous recombination to stably integrate the sequences of the invention into the genome organism are encompassed by the invention. The invention is particularly directed to methods where sequences of the invention are utilized to alter the growth of an organism. Such methods encompass use of the sequences of the invention to interfere with the function or synthesis of a P-glycoprotein that controls growth of an organism.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The present invention may be used for transformation of any plant species, including, but not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pin us contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Preferably, plants of the present invention are crop plants (for example, rice, corn, alfalfa, sunflower, *Brassica*, soybean, cotton, safflower, peanut, sorghum, wheat, millet, tobacco, etc.), more preferably corn, rice and sorghum plants.

The invention is drawn to compositions and methods for increasing the resistance of a plant to a pathogen. Accordingly, the compositions and methods are also useful in protecting plants against fungal pathogens, viruses, nematodes, insects, acarids and the like.

By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened. The methods of the invention can be utilized to protect plants from disease, particularly those diseases that are caused by plant pathogens.

By "antipathogenic compositions" is intended that the compositions of the invention have antipathogenic activity and thus are capable of suppressing, controlling, and/or killing the invading pathogenic organism. An antipathogenic composition of the invention will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference).

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Specific fungal and viral pathogens for the major crops include: Soybeans: *Phytophthora megasperma* fsp. *glycinea*, *Macrophomina phaseolina*, *Rhizoctonia solani*, *Sclerotinia sclerotiorum*, *Fusarium oxysporum*, *Diaporthe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Septoria glycines*, *Phyllosticta sojicola*, *Alternaria alternata*, *Pseudomonas syringae* p.v. *glycinea*, *Xanthomonas campestris* p.v. *phaseoli*, *Microsphaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium debaryanum*, Tomato spotted wilt virus, *Heterodera glycines Fusarium solani*; Canola: *Albugo candida*, *Alternaria brassicae*, *Leptosphaeria maculans*, *Rhizoctonia solani*, *Sclerotinia sclerotiorum*, *Mycosphaerella brassiccola*, *Pythium ultimum*, *Peronospora parasitica*, *Fusarium roseum*, *Alternaria alternata*; Alfalfa: *Clavibater michiganese* subsp. *insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medicaginis* var. *medicaginis*, *Cercospora medicaginis*, *Pseudopeziza medicaginis*, *Leptotrochila medicaginis*, *Fusarium*, *Xanthomonas campestris* p.v. *alfalfae*, *Aphanomyces euteiches*, *Stemphylium herbarum*, *Stemphylium alfalfae*; Wheat: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f.sp. *tritici*, *Puccinia graminis* f.sp. *tritici*, *Puccinia recondita* f.sp. *tritici*, *Puccinia striiformis*, *Pyrenophora tritici-repentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea*, *Tilletia tritici*, *Tilletia laevis*, *Ustilago tritici*, *Tilletia indica*, *Rhizoctonia solani*, *Pythium arrhenomannes*, *Pythium gramicola*, *Pythium aphanidermatum*, High Plains Virus, European wheat striate virus; Sunflower: *Plasmophora halstedii*, *Sclerotinia sclerotiorum*, Aster Yellows, *Septoria helianthi*, *Phomopsis helianthi*, *Alternaria helianthi*, *Alternaria zinniae*, *Botrytis cinerea*, *Phoma macdonaldii*, *Macrophomina phaseolina*, *Erysiphe cichoracearum*, *Rhizopus oryzae*, *Rhizopus arrhizus*, *Rhizopus stolonifer*, *Puccinia helianthi*, *Verticillium dahliae*, *Erwinia carotovorum* pv. *carotovora*, *Cephalosporium acremonium*, *Phytophthora cryptogea*, *Albugo tragopogonis*; Corn: *Fusarium moniliforme* var. *subglutinans*, *Erwinia stewartii*, *Fusarium moniliforme*, *Gibberella zeae* (*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella-maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia carotovora*, Corn stunt spiroplasma, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maze Streak Virus, Maize Stripe Virus, Maize Rough Dwarf Virus; Sorghum: *Exserohilum turcicum*, *Colletotrichum graminicola* (*Glomerella graminicola*), *Cercospora sorghi*, *Gloeocercospora sorghi*, *Ascochyta sorghina*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Perconia circinata*, *Fusarium moniliforme*, *Alternaria alternata*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari*, *Sporisorium reilianum* (*Sphacelotheca reiliana*), *Sphacelotheca cruenta*, *Sporisorium sorghi*, Sugarcane mosaic H, Maize Dwarf Mosaic Virus A & B, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium oxysporum*, *Pythium arrhenomanes*, *Pythium graminicola*, etc.

Nematodes include parasitic nematodes such as root-knot, cyst, and lesion nematodes, including *Heterodera* and *Globodera* spp; particularly *Globodera rostochiensis* and *globodera pailida* (potato cyst nematodes); *Heterodera glycines* (soybean cyst nematode); *Heterodera schachtii* (beet cyst nematode); and *Heterodera avenae* (cereal cyst nematode).

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); Popilliajaponica, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

The following examples are offered by way of illustration and not by way of limitation.

EXAMPLE 1

Mapping the Location of br2 on Chromosome 1 L

Previous genetic studies revealed that br2 was located on maize chromosome 1L within 0.1 cM of hm1. In an $F_2$ population of 1500 plants between the br2 recombinant mutant tester (br2br2Hm1Hm1) and Pr (a maize inbred homozygous recessive at the hm1 locus; Br2hm1hm1), only one recombinant (hm1hm1br2br2) was found between br2 and hm1. However, the orientation of these two genes in relation to each other was not determined. To address whether br2 is proximal or distal to hm1, the progeny of the above recombinant and its progenitors was RFLP genotyped using probes from the hm1 gene as well as two RFLP markers, PIO200644 and PIO200044. These DNA markers flank hm1, with PIO200644 and PIO200044 mapping 5 cM proximal and distal to hm1, respectively (Johal et al. (1992) *Science* 258:985-987). The PIO200044 allele of the recombinant tester was the same as the original br2 tester whereas the hm1 and PIO200644 alleles had recombined, indicating that br2 is localized in between hm1 and PIO200044.

EXAMPLE 2

Transposon Tagging and Cloning of br2

To clone the wild-type Br2 gene, a directed (targeted) tagging approach was used in which Robertson's Mutator (Mu) was used as the genetic mutagen (Robertson (1978) *Mutation Res.* 51:21-28; Walbot (1992) *Annu. Rev. Plant Physiol. Plant Mol. Biol.* 43:49-82). Crosses were made between Mu-containing Br2/Br2 females and the recombinant mutant tester (described in Example 1) containing the br2 reference (br2-ref) allele. A total of 90,000 hybrid plants from the resulting F1 population were planted in the field that yielded 35 dwarf plants. These putative br2 mutants were propagated by crossing with B73 (an inbred) females as well as by backcrossing to the br2 tester. The latter set of crosses, which essentially tested allelism between br2-ref and the new brachytic mutant alleles, was performed to evaluate which of the 35 new mutants were heritable and not caused by environmental factors. The brachytic stature of maize plants can be mimicked by plants that are inflicted with Stewart's wilt, a bacterial disease caused by *Erwinia stewartii*. The results obtained from the allelism test eventually allowed the selection of 11 genuine br2 mutants, which were designated br2-1 through br2-11.

In an effort to advance these potentially Mu-tagged mutants for co-segregation analysis, the outcross progeny of each mutant with B73 was genotyped with probes from hm1 and PIO200044. This assisted in the identification of plants from each progeny that inherited the tagged mutant allele. A few of such plants were backcrossed with the br2 tester, and it resulted in the production of populations from each mutant that segregated 1:1 for plants containing and lacking the tagged mutant allele. Since only the brachytic plants from these populations contained the tagged mutant allele, this backcrossing scheme alleviated the need of using molecular markers for tracking down the inheritance of the tagged alleles.

A DNA gel blot analysis was used to search for Mu elements that may have caused these mutant alleles. The brachytic and tall plants from each family were compared with each other on a Southern blot hybridized with each of the nine Mu elements (Bennetzen et al. (1993) Crit. Rev. Plant Sci. 12:57-95). This analysis resulted in the identification of a Mu8-hybridizing restriction fragment from each of two mutants, br2-5 and br2-6, that segregated completely with the mutant allele in more than 80 progeny plants. While the size of the Mu8-hybridizing XhoI fragment was ~7.5 kb in the br2-5 mutant allele, it was ~9.0 kb in br2-6. Strangely, however, a ~9.0 kb XhoI restriction fragment that cosegregated with the mutant allele of br2-6 also hybridized to a Mu7-specific probe. However, following cloning, it was realized that both Mu8- and Mu7-specific probes hybridized to the same XhoI restriction fragment. The 7.5 kb XhoI fragment that hybridized to Mu8 in br2-5 was also cloned. Both of these clones were subsequently subcloned and partially sequenced.

Sequence comparisons revealed that both end sequences and the XhoI sites of these clones were identical indicating that they had originated from the same region of the maize genome. The comparisons also revealed that the Mu8-homologous regions of both subclones were identical, both in size and sequence, indicating that the source of restriction fragment length polymorphism was due to variation elsewhere within the clones. Further sequence analyses revealed the sources of the polymorphism. In br2-6, an insertion of a 2.1 kb Mu7 element located 510 bp downstream of the 5'-end XhoI site was found (FIG. 1). Since this insertion is in exon 1, albeit only nine bp from the exon/intron junction, it is expected to disrupt the function of the br2 gene. In br2-5, a novel insertion in intron 4 was discovered (FIG. 1). This insertion, which has characteristics of a transposable element, may or may not have interfered with the function of the gene.

The Mu8-homologous region of both clones spanning nucleotides 4569 to 5472 (880 bp) from the 5' end coincided with nucleotides 276 to 1163 of Mu8, and the two showed a sequence identity of 94%. No terminal inverted repeats (TIRs) of Mu, however, were found to flank the Mu8-homologous DNA in either clone, raising questions concerning the source or origin of this DNA. That it did not result from a Mu8-insertional event became obvious when a BLAST analysis was conducted with this sequence. The homology search clearly demonstrated that the Mu8-homologous region of the cloned gene is its bona fide part. Apparently, this sequence was somehow hijacked by a Mu element, that later recombined to create element number 8 (Mu8) of the Mutator system.

To determine if the br2 gene had been cloned, or instead some natural polymorphism that was tightly linked with br2, a reverse genetics approach involving PCR that relies on identifying Mu insertions in additional mutations of a candidate gene was used. This approach, which was previously utilized to verify the cloning of two separate genes, lls1 (Gray et al., (1997) Cell 89:25-31) and Les22 (Hu et al. (1998) Plant Cell 10:1095-1105), is based on the premise that in independent mutations, multiple Mu insertions in the vicinity of a cloned gene can only be found, if the insertions are causally involved in the generation of these mutations (Walbot (1992) Annu. Rev. Plant Physiol. Plant Mol. Biol. 43:49-82).

To execute this experiment, two oppositely oriented, gene-specific primers were designed from the region 5' of Mu7 insertion in br2-6. This region of the gene was targeted because Mu elements tend to insert in the 5' end of genes (Bennetzen et al. (1993) Crit. Rev. Plant Sci. 12:57-95). Each primer was used in combination with a Mu TIR-specific primer to amplify DNA using PCR from each of the other nine br2 mutants. Amplification products that hybridized with a gene-specific probe from the 5' end were obtained from the DNA of two mutants, br2-3 and br2-9. These PCR products were cloned and sequenced, and it revealed that Mu elements had inserted in br2-3 and br2-9 at locations 269 and 394 nucleotides, respectively, from the Mu7 insertion site in br2-6. Thus, three insertions that were within 400 nucleotides of each other in three independent br2 mutants were identified. These results strongly suggested that br2 had been cloned. The fact that the Mu7/Mu8-hybridizing 9.0 kb XhoI fragment was missing in the progenitor of br2-6 further substantiated this interpretation.

An additional piece of evidence for the correct cloning of br2 came from the molecular analysis of two tall revertants, both of which were isolated from the br2-ref allele. These revertants were identified during an experiment conducted to generate a new tester of maize with four recessive genetic markers, namely hm1, br2, hm2 (a duplicate of hm1, conferring adult plant resistance to C. carbonum race 1; Multani et al. (1998) Proc. Natl. Acad. Sci. USA 95:1686-1691, and bk2 (plants homozygous recessive for this gene have brittle stalks and leaves; Coe et al. (1988) Corn & Corn Improvement, G. F. Sprague (ed.), Madison, Wis.). Thus, these tall revertants were marked with hm1, hm2 and bk2, all of which are rare in the maize germplasm. A southern blot analysis was performed to seek whether these revertants had undergone any DNA polymorphism at or near the cloned region. The DNA of these revertants was restriction mapped with a number of enzymes and compared with that of the progenitor and a number of maize inbreds, including all that are susceptible to C. carbonum. A unique RFLP was detected in both revertants that was missing in their progenitor as well as in all maize inbreds that were tested in this experiment. Since this polymorphism is identical in both revertants, these results indicate that either these revertants are the result of the same molecular event, or that a similar molecular event is required for the functional reversion of the br2-ref allele. It is unlikely that these revertants were the result of pollen contamination, because both revertants were brittle and susceptible to C. carbonum race 1, and they also possessed the same hm1 and hm2 RFLPs as that of their progenitor. The exact molecular nature of the event(s) that led to these revertants remains to be investigated, as is the nature of the mutation in the br2-ref allele.

EXAMPLE 3

Identity of the Br2 Gene and the Protein it Encodes

To ascertain the molecular nature of Br2, both XhoI clones were fully sequenced. This allowed the compilation an approximately 7.0 kb stretch of the genomic region of the br2 locus that appears to contain more than 90% of the Br2 coding region (SEQ ID NO: 1). When this sequence was subjected to BLAST analysis, it revealed that the predicted br2 protein has an extensive sequence and structural similarity with the multidrug-resistance (MDR)-like gene-encoded P-glycoproteins (Gottesman et al. (1995) *Annu. Rev. Genet.* 29:607-649; Borst et al. (1997) *Trends Genet.* 13:217-222; Croop (1998) *Methods Enzym.* 292:101-116). The products of the MDR-like genes belong to the family of ATP-binding cassette-containing (ABC) transporters that mediate the ATP-driven transmembrane translocation a large variety of substrates (Gottesman et al. (1995) *Annu. Rev. Genet.* 29:607-649; Higgins (1992)) *Annu. Rev. Cell Biol.* 8:67-113). More than 67% amino acid sequence identity was observed between br2 and the predicted protein of the *Arabidopsis* P-glycoprotein gene, AtPGP1 (Dudler et al. (1992) *J. Biol. Chem.* 267:5882-5888). AtPGP1, which was the first P-glycoprotein gene to be cloned from plants, was isolated on the basis of its homology with the human MDR1 gene, with which it shares 41% identity (Dudler et al. (1992) *J. Biol. Chem.* 267:5882-5888). Three other P-glycoprotein genes have since been cloned from *Arabidopsis* (Dudler et al. (1998) *Methods Enzym.* 292:162-173, barley (Davies et al. (1997) *Gene* 199:195-202) and potato (Wang et al. (1996) *Plant Mol. Biol.* 31:683-687). However, all of these genes were identified molecularly, and in no case, including AtPGP1, is it known what the actual in planta function(s) of these genes might be. Thus, BR2 is the first plant P-glycoprotein where there is clear evidence for its function. Furthermore, BR2 is the first P-glycoprotein from any organism that is known to be involved in controlling the growth or development of an organism.

BR2 may also be involved in plant defense responses against pathogens. When grown under greenhouse conditions, br2 mutants display an increased incidence of buggy whip, a disease-like necrotic condition of the growing tip that mimics bacterial-induced necroses. The involvement of P-glycoproteins in defense against a toxin produced by a *Pseudomonas aeruginosa* strain which infects both plants and animals has recently been demonstrated (Mahajan-Miklos et al. (1999) *Cell* 96:47-56).

In contrast to the *Arabidopsis* AtPGP1 gene, which contains 10 exons and 9 introns, the maize Br2 gene contains 5 exons and 4 introns, although the locations and exon/intron boundaries of these 4 introns are identical to the corresponding introns from the *Arabidopsis* AtPGP1 gene. The structural organization of the barley and potato P-glycoprotein genes has not yet been elucidated. SEQ ID NO: 2 represents the full-length Br2 cDNA that was isolated from ten-day-old B73 seedlings in four overlapping parts by a combination of RT-PCR and 3'-RACE.

A BLAST analysis of the Br2 genomic sequence (SEQ ID NO: 1) revealed that Br2 was most closely related to an mRNA sequence for a potato P-glycoprotein (EMBL Accession No: Y10099). Ignoring the Mu8-homologous region of Br2 (SEQ ID NO: 1), the longest stretch of nucleotide sequence identity was 29 nucleotides with an mRNA sequence from a mouse multidrug resistant protein (GenBank Accession No: M14757).

EXAMPLE 4

Transformation of Maize by Particle Bombardment and Regeneration of Transgenic Plants Immature maize embryos from greenhouse donor plants are bombarded with a plasmid containing a P-glycoprotein nucleotide sequence of the invention operably linked to a promoter that drives expression in a plant and the selectable marker gene PAT (Wohlleben et al. (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the P-glycoprotein nucleotide sequence of the invention operably linked to the plant promoter of interest is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for dwarf phenotype or other phenotype associated with expression of the P-glycoprotein nucleotides sequence of the invention.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H$_2$O following adjustment to pH 5.8 with KOH); 2.0 g/l Gelrite (added after bringing to volume with D-I H$_2$O); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-1H$_2$O following adjustment to pH 5.8 with KOH); 3.0 g/l Gelrite (added after bringing to volume with D-I H$_2$O); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H$_2$O) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I H$_2$O after adjusting to pH 5.6); 3.0 g/l Gelrite (added after bringing to volume with D-I H$_2$O); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H$_2$O), 0.1 g/l myo-inositol, and 40.0 g/l sucrose (brought to volume with polished D-I H$_2$O after adjusting pH to 5.6); and 6 g/l bacto-agar (added after bringing to volume with polished D-I H$_2$O), sterilized and cooled to 60° C.

EXAMPLE 5

*Agrobacterium*-Mediated Transformation of Maize and Regeneration of Transgenic Plants For *Agrobacterium*-mediated transformation of maize with a P-glycoprotein nucleotide sequence of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of *Agrobacterium*, where the bacteria are capable of transferring the P-glycoprotein nucleotide sequence of the invention to at least one cell of at least one of the immature embryos (step 1: the infection step). In this step the immature embryos are preferably immersed in an *Agrobacterium* suspension for the initiation of inoculation. The embryos are co-cultured for a time with the *Agrobacterium* (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). Preferably the immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated protein comprising the amino acid sequence set forth in SEQ ID NO: 3.

2. An isolated protein comprising an amino acid sequence having at least 85% identity to the amino sequence set forth in SEQ ID NO: 3, wherein said protein is a P-glycoprotein that functions to control plant height.

3. The isolated protein of claim 2, wherein said amino acid sequence has at least 90% identity to the amino sequence set forth in SEQ ID NO: 3.

4. The isolated protein of claim 2, wherein said amino acid sequence has at least 95% identity to the amino sequence set forth in SEQ ID NO: 3.

5. An isolated protein comprising a fragment of SEQ ID NO: 3, wherein said wherein said fragment that functions to control plant height and said fragment consists of at least 250 contiguous amino acids of the amino acid sequence set forth in SEQ ID NO: 3.

6. The isolated protein of claim 5, wherein said fragment consists of at least 500 contiguous amino acids of the amino acid sequence set forth in SEQ ID NO: 3.

* * * * *

UNITED STATES PATENT AND TRADEMARK OFFICE
CERTIFICATE OF CORRECTION

PATENT NO. : 7,276,584 B1 Page 1 of 1
APPLICATION NO. : 11/338199
DATED : October 2, 2007
INVENTOR(S) : Johal et al.

It is certified that error appears in the above-identified patent and that said Letters Patent is hereby corrected as shown below:

Column 58
Line 55: "wherein said wherein said fragment that functions"

should read

--wherein said fragment functions--

Signed and Sealed this

Third Day of February, 2009

JOHN DOLL
*Acting Director of the United States Patent and Trademark Office*

SEQUENCE LISTING

```
<160> NUMBER OF SEQ ID NOS: 3

<210> SEQ ID NO 1
<211> LENGTH: 8036
<212> TYPE: DNA
<213> ORGANISM: Zea mays
<220> FEATURE:
<221> NAME/KEY: unsure
<222> LOCATION: (371)
<223> OTHER INFORMATION: n at position 371 can be an a, g, c, or t.
<220> FEATURE:
<221> NAME/KEY: unsure
<222> LOCATION: (297)
<223> OTHER INFORMATION: n at position 297 can be an a, g, c, or t.
<220> FEATURE:
<221> NAME/KEY: unsure
<222> LOCATION: (400)
<223> OTHER INFORMATION: n at position 400 can be an a, g, c, or t.
<220> FEATURE:
<221> NAME/KEY: unsure
<222> LOCATION: (725)
```

<223> OTHER INFORMATION: n at position 725 can be an a, g, c, or t.
<220> FEATURE:
<221> NAME/KEY: unsure
<222> LOCATION: (856)
<223> OTHER INFORMATION: n at position 856 can be an a, g, c, or t.

<400> SEQUENCE: 1

| | | | | |
|---|---|---|---|---|
| ctttcaatta | agttgagtcg | ggggtagatt | ctcaaggcta | cataaatagt | ttttttcta | 60 |
| gaatggatgc | atttgtttaa | gagaaaaatg | atgcacttgg | atgcatcaag | caaagggatg | 120 |
| taagaatgtt | gaaaaaacac | atgacccgta | tcggcgagat | gcttatttat | ccattctta | 180 |
| tcacagggat | gcatatgcaa | caaaaccaaa | acagatggtt | agcgagtgac | agtatataga | 240 |
| gatctaaagt | tgtccgacac | ttcatcggta | aaaaagcag | cataaccgag | tgaatgnaag | 300 |
| aaaaacgaat | ttctcatata | cacagcaggt | tttcttaaaa | acgttatat | cggtattata | 360 |
| ttaagaagag | nccaaaatat | ggtcctgtcg | agaaattn | taaacattag | ttctcatcac | 420 |
| cagtgagccg | tcaccatcta | gtttgcaacg | gtccagttag | agtgcactca | ggactcgcag | 480 |
| cgagagaatt | ttttaatca | agcctaaaat | tcactttcgg | acaaatcgaa | ctactcataa | 540 |
| atattaacca | tgagacctt | tcgccgcagc | aggttttcta | tcggccgtta | gattttagtg | 600 |
| acgatgaaaa | tgatagaacg | caacgtgccg | catgcatcca | ttcccattcg | ttttccacag | 660 |
| tacatgtagg | agtactgtgc | aagtagggtc | cgtacattca | gtctctctca | ctagttggat | 720 |
| tcttntaatg | ctacaaagac | atgagctgcc | gggaatggga | accggaggag | cgagcgagcc | 780 |
| tggcggtctc | acacacacag | tcacactccc | aagccaatta | ttataagagg | ggagatgagc | 840 |
| aactccagct | cttaanccaa | tccactcctc | ctccctctcc | acctcatatg | ctttgctctg | 900 |
| ccactctgct | gaggtggggg | gcagaggagc | tcccctccc | tcctctcccc | tcctcgccat | 960 |
| gtctagcagc | gacccggagg | agatcagggc | gcgcgtcgtc | gttctcggtt | cgccccatgc | 1020 |
| cgacggcggc | gacgagtggg | cccggcccga | gctcgaggcc | ttccatctgc | cgtctcccgc | 1080 |
| ccaccagcct | cctggcttcc | tagccgggca | accggaagca | gcagagcaac | ccacgctccc | 1140 |
| tgctcctgct | ggccgcagca | gcagcagcag | caacacgcct | actacatctg | ccggtggcgg | 1200 |
| cgctgctcct | cctcctcctt | cttcgcctcc | ccctccgccg | gcttctctgg | agaccgagca | 1260 |
| gccgcccaat | gccaggccag | cctccgccgg | cgccaatgac | agcaagaagc | ccaccccgcc | 1320 |
| cgccgccctg | cgcgacctct | tccgcttcgc | cgacggcctc | gactgcgcgc | tcatgctcat | 1380 |
| cggcacccctc | ggcgcgctcg | tccacgggtg | ctcgctcccc | gtcttcctcc | gcttcttcgc | 1440 |
| cgacctcgtc | gactccttcg | gctcccacgc | cgacgacccg | gacaccatgg | tccgcctcgt | 1500 |
| cgtcaagtac | gccttctact | tcctcgtcgt | cggagcggca | atctgggcat | cctcgtgggc | 1560 |
| aggtacgcta | tccctcctcc | tcctgccgcc | ccagcttgtg | tgcgtcgcga | attggcggtc | 1620 |
| aatttggatt | ggatgacaaa | tcacgtcggt | cagccaatcg | ccgtggctac | aaacgagatg | 1680 |
| ttcaaatcgt | tcgccccgct | cgcaagagat | ctcttgctgg | atgtggaccg | gcgagcggca | 1740 |
| gtcgacgcgg | atgcggattc | ggtacctgga | cgcggcgctg | cggcaggacg | tgtccttctt | 1800 |
| cgacaccgac | gtgcgggcct | cggacgtgat | ctacgccatc | aacgcggacg | ccgtggtggt | 1860 |
| gcaaggacgc | catcagccag | aaactgggca | acctcatcca | ctacatggcc | accttcgtgg | 1920 |
| ccggcttcgt | cgtggggttc | acggccgcgt | ggcagctggc | gctggtcacg | ctggccgtgg | 1980 |
| tgccgctcat | cgccgtcatc | ggcgggctga | gcgccgccgc | gctcgccaag | ctctcgtccc | 2040 |
| gcagccagga | cgcgctctcg | ggccgcagcg | gcatcgcgga | gcaggcgctc | gcgcagatac | 2100 |
| ggatcgtgca | ggcgttcgtt | ggcgaggagc | gcgagatgcg | ggcctactcg | gcggcgctgg | 2160 |

-continued

```
ccgtggcgca gaggatcggc taccgcagcg gcttcgccaa ggggctcggc ctcggcggca    2220
cctacttcac cgtcttctgc tgctacgggc tcctgctctg gtacggcggc cacctcgtgc    2280
gcgcccagca caccaacggc gggctcgcca tcgcaccatg ttctccgtca tgatcggcgg    2340
actgtaaggc ccaccacacc acgcactctc tccttctgct gtcctcggcc gccccgtcg     2400 tcattgctgc tgacggtatc tgtggatcgc gtgcagggcc ctcggcagtc ggcgccgagc    2460
atggccgcgt tcgccaaggc gcgtgtggcg gctgccaaga tcttccgcat catcgaccac    2520
aggccgggca tctcctcgcg cgacggcgcg agccagagt cggtgacggg gcgggtggag     2580
atgcggggcg tggacttcgc gtacccgtcg cggccggacg tccccatcct gcgcggcttc    2640
tcgctgagcg tgcccgccgg gaagaccatc gcgctggtgg gcagctccgg ctccgggaag    2700
agcacggtgg tgtcgctcat cgagagattc tacgacccca gcgcaggtat acctagtact    2760
gttactactt ttagcgcatt aatctgagga tgtccagttc gcttgcttgc caatcgccat    2820
tgccatcgca acaacaatac ttcgccaact gccattgctg ggtagattag tacagtagca    2880
gttagaagaa gcctccactg tacattgcat tgccaaacaa agtgaattg tgcagtaact     2940 ctgtaccacc acattgacat ggaaatgaag tgaatgcttg gagcatgcag agctggccgg    3000
cctcatgggc tgctgctacc tgctagctag ccaaccagaa ccagccatcc tctttcttgc    3060
ttttcttttt actttctttg gtcgtggctg tttgtggtca tacatacatt cacgcagagc    3120
agaagagcta gctaagctag gtgggtgtgc ctgcaacgcg ggacaaagaa aactatttgt    3180
tgcctggcaa gatgctactg ttgcctagca catgcctgcc attgaccgac tgctcagtga    3240
gaagtggttc agttgtgctg ttgacagtat agatagatat atatagtagc cctgtagatt    3300 ttttttttcag acaaaaaaag aagaagaacg agatgaagtc tgcaattcgg ttttggcagg   3360
gcaaatcctg ctggacgggc acgacctcag gtcgctggag ctgcggtggc tgcggcggca    3420
gatcgggctg gtgagccagg agccggcgct gttcgcgacg agcatcaggg agaacctgct    3480
gctggggcgg gacagccaga gcgcgacgct ggcggagatg gaggaggcgg ccagggtggc    3540
caacgcccac tccttcatca tcaaactccc cgacggctac gacacgcagg tccgtcccgt    3600
atagctagct cactagctgc actgccactt ctctcgcttg ctcccccacc gttgctgcct    3660
gttgctctcc aatccacttg tcggtgtctg gaccacacgt gctgcttgcc tagctgctcc    3720
acatctgctt tccctgtcca accttatgca actcactcta atactatatc aaatacattt    3780
ctagagttta aagcttatct tagaataaat gcatctttag ctacgagaca acctaacttc    3840
agttgttgtt gttgtttttt ttactttctc tcttctcaca aatactatga ttacgtcttt    3900
acagcgatct tttttattcc aaacctaaaa atgcatgcac tcactctaaa agcgcaaagg    3960
gagcatcttt ttttccccca tcatctgcac gcagccttt cttttcctca tgtcacgaag     4020
ggactgaagg tgtgtatgca gcgtcaagtc atccatccgt tccactccac tcactcatgc    4080
gtcgcgcact ctgcgctcgt gcctgcccgg ggctaaagct ttagtagcta gcctcagatc    4140
agatactgtt cgtgtttgtt aggccgcggc agctgcacat gagctcatga cagccggcag    4200
caccaccacc aacgccatgg aagaggggtc ggggtccatc acatagacat aatgcctgtt    4260
gtagactagg acgggagggc aattgttagg cgcctgttgc catcgcattt gctgctgtgg    4320
gttgccaaca agtaacatgc caggatgctt tgctatcacg cacaggacag agaggtcct     4380 ttttctcgac acaagctcta cagcctctac taaactagca cttgctgatg agtgcagagg    4440
atgaatggac gatgaacatc tagagtgaga gagaaaaaaa tgttaataat aataaaaagt    4500
```

-continued

| | |
|---|---|
| agtagcagga ttaagaatca acctggggta cgtaggaaga ggtacaatcc ctaggaatct | 4560 |
| agagtatgag aagtatggga ggagttgggg gagtgaaacg gaacaaattc cgagttggta | 4620 |
| ttttgtcggg aatgtcaagt tgattttttga tcctagtgca agcaagaatt atcaatcact | 4680 |
| cagactcagc ctgtctgtgt ctgtccaccc cagctcttgc tactctactt actactgtgc | 4740 |
| tactagtggg tagggtaggt atcttacata aactgttatt ataaactgtc atctgagaaa | 4800 |
| gagagccagt caaacccatg ctgctgctta ttttaatcac tgtcaaatgg caggcaggca | 4860 |
| ggcagtctgg ttagttaata acatctggga agggtttaat caaaccaaat caaatcagac | 4920 |
| gaaatctaga ggccacatgg gatggggcca tatgtactgt actagcataa ctagcggcta | 4980 |
| gattttatta gaacacggac tcacactccc ataactataa ctgacttgat catgattcct | 5040 |
| tgccaagcaa tgctcgcatg cccatgcatg catcatccct ggtcaaactc aaacactctc | 5100 |
| caccgtcagg gaataagact tattatttta ttaacaattc aattttttatt tattaattac | 5160 |
| gtctggacga ggagtactgg tttatttgat gagagacatg gcagtccaag tcaaactcgt | 5220 |
| ttgtctgacc atggcggtga tggccggtgc aggttgggga gcgcggcctg cagctctccg | 5280 |
| gtgggcagaa gcagcgcatc gccatcgccc gcgccatgct caagaacccc gccatcctgc | 5340 |
| tgctggacga ggccaccagc gcgctggact ccgagtctga aagctcgtg caggaggcgc | 5400 |
| tggaccgctt catgatgggg cgcaccaccc ttggtgatcg cgcaacaggc tgtccaccat | 5460 |
| ccgcaaaggc cgacgtggtg gccgtgctgc agggcggcgc cgtctccgag atgagcgcgc | 5520 |
| acgacgagct gatggccaag ggcgagaacg gcacctacgc caagctcatc cgcatgcagg | 5580 |
| agcaggcgca cgaggcggcg ctcgtcaacg cccgccgcag cagcgccagg ccctccagcg | 5640 |
| cccgcaactc cgtcagctcg cccatcatga gcgcaactc ctcctacggc cgctccccct | 5700 |
| actcccgccg cctctccgac ttctccacct ccgacttcac cctctccatc cacgacccgc | 5760 |
| accaccacca ccgaccatg gcggacaagc agctggcgtt ccgcgccggc gccagctcct | 5820 |
| tcctgcgcct cgccaggatg aactcgcccg agtgggccta cgcgctcgcc ggctccatcg | 5880 |
| gctccatggt ctgcggctcc ttcagcgcca tcttcgccta catcctcagc gccgtgctca | 5940 |
| gcgtctacta cgcgccggac ccgcggtaca tgaagcgcga gatcgcaaaa tactgttacc | 6000 |
| tgctcatcgg catgtcctcc gcggcgctgc tgttcaacac ggtgcagcac gtgttctggg | 6060 |
| acacggtggg cgagaacttg accaagcggg tgcgcgagaa gatgttcgcc gccgtgttcc | 6120 |
| gcaacgagat cgcctggttc gacgcggacg agaacgccag cgcgcgcgtg accgccaggc | 6180 |
| tagcgctgga cgcccagaac gtgcgctccg ccatcgggga ccgcatctcc gtcatcgtcc | 6240 |
| agaactcggc gctgatgctg gtggcctgca ccgcggggtt cgtcctccag tggcgcctcg | 6300 |
| cgctcgtgct cctcgccgtg ttcccgctcg tcgtgggcgc caccgtgctg cagaagatgt | 6360 |
| tcatgaaggg cttctcgggg gacctggagg ccgcgcacgc cagggccacg cagatcgcgg | 6420 |
| gcgaggccgt ggccaacctg cgcaccgtgg ccgcgttcaa cgcggagcgc aagatcacgg | 6480 |
| ggctgttcga ggccaacctg cgcggcccgc tccggcgctg cttctggaag gggcagatcg | 6540 |
| ccggcagcgc ctacgcgtg gcgcagttcc tgctgtacgc gtcctacgcg ctggggctgt | 6600 |
| ggtacgcggc gtggctggtg aagcacggcg tgtccgactt ctcgcgcacc atccgcgtgt | 6660 |
| tcatggtgct gatggtgtcc gcgaacggcg ccgccgagac gctgacgctg gcgcggact | 6720 |
| tcatcaaagg cgggcgcgcg atgcggtcgg tgttcgagac aatcgaccgc aagacggagg | 6780 |
| tggagcccca cgacgtggac gcggcgccgg tgccggacgg cccaggggcg aaggtggaac | 6840 |
| ttaagcacgt ggactttttg tacccgtcgc ggccggacat ccaagtgttc cgcgacctga | 6900 |

```
gcctccgtgc gcgcgccgga aaaacgttgg cgctggtggg gccgagcggg tccggcaaga    6960
gctcggtcct ggctctggtg cagcggttct acaagcccac gtccgggcgc gtgctcttgg    7020
acggcaagga cgtgcgcaag tacaacctgc gggcgctgcg gcgcgtggtg gcggtggtac    7080
cgcaggagcc gttcctgttc gcggcgagca tccacgagaa catcgcgtac gggcgcgagg    7140
gcgcgacgga ggcggaggtg gtggaggcgg cggcgcaggc gaacgcgcac cggttcatcg    7200
cggcgctgcc ggaggggtac cggacgcagg tgggcgagcg cggggtgcag ctgtcggggg    7260
ggcagcggca gcggatcgcg atcgcgcgcg cgctggtgaa gcaggcggcc atcgtgctgc    7320
tggacgaggc gaccagcgcg ctggacgccg agtcggagcg gtgcgtgcag gaggcgctgg    7380
agcgcgcggg gtccgggcgc accaccatcg tggtggcgca ccggctggcc acggtgcgcg    7440
gcgcgcacac catcgcggtc atcgacgacg caaggtggc ggagcagggg tcgcactcgc    7500
acctgctcaa gcaccatccc gacgggtgct acgcgcggat gctgcagctt gcagcggctg    7560
acgggcgcgg cggccgggcc cgggccgtcg tcctcgtgca acggggccgc gtaggacgga    7620
atggatggat ggatgggttt ggttcctcga gagattgatg ggtgaggaag ctgaagctcc    7680
ggatcaaatg gtggtactcc atgatcgcaa caatgagggg aaaaaaggaa aggagaaaat    7740
acggtggttc atatgattgt acaatttgac gatctgtttg agtcggggtt ttaggatgat    7800
gtaaaccttc actcgccttt tttttactct tgtttctcat ccgcatcagt atcatctatc    7860
tacatacagt gtcagagatg ggaactgatc ccgcatcatc atctacctcc caaggcaccc    7920
cagattgtat taatgtactt agttagcctg tttatatat acttataagt accaaatagc    7980
agaattttac tccttatctg cagtagcacg aaagaaaaaa aaaaaaagct aaacct        8036
```

<210> SEQ ID NO 2
<211> LENGTH: 4653
<212> TYPE: DNA
<213> ORGANISM: Zea mays
<220> FEATURE:
<221> NAME/KEY: CDS
<222> LOCATION: (91)..(4272)

<400> SEQUENCE: 2

```
ctcctccctc tccacctcct atgctttgct ctgccactct gctgaggtgg ggggagagga     60
gctccccctc cctcctctcc cctcctcgcc atg tct agc agc gac ccg gag gag    114
                                   Met Ser Ser Ser Asp Pro Glu Glu
                                     1               5 atc agg gcg cgc gtc gtc gtt ctc ggt tcg ccc cat gcc gac ggc ggc    162
Ile Arg Ala Arg Val Val Val Leu Gly Ser Pro His Ala Asp Gly Gly
 10                  15                  20 gac gag tgg gcc cgg ccc gag ctc gag gcc ttc cat ctg ccg tct ccc    210
Asp Glu Trp Ala Arg Pro Glu Leu Glu Ala Phe His Leu Pro Ser Pro
 25                  30                  35                  40 gcc cac cag cct cct ggc ttc cta gcc ggg caa ccg gaa gca gca gag    258
Ala His Gln Pro Pro Gly Phe Leu Ala Gly Gln Pro Glu Ala Ala Glu
                 45                  50                  55 caa ccc acg ctc cct gct cct gct ggc cgc agc agc agc agc agc aac    306
Gln Pro Thr Leu Pro Ala Pro Ala Gly Arg Ser Ser Ser Ser Ser Asn
             60                  65                  70 acg cct act aca tct gcc ggt ggc ggc gct gct cct cct cct cct tct    354
Thr Pro Thr Thr Ser Ala Gly Gly Gly Ala Ala Pro Pro Pro Pro Ser
         75                  80                  85 tcg cct ccc cct ccg ccg gct tct ctg gag acc gag cag ccg ccc aat    402
Ser Pro Pro Pro Pro Ala Ser Leu Glu Thr Glu Gln Pro Pro Asn
     90                  95                 100
```

-continued

| | |
|---|---|
| gcc agg cca gcc tcc gcc ggc gcc aat gac agc aag aag ccc acc ccg<br>Ala Arg Pro Ala Ser Ala Gly Ala Asn Asp Ser Lys Lys Pro Thr Pro<br>105               110                    115                  120 | 450 |
| ccc gcc gcc ctg cgc gac ctc ttc cgc ttc gcc gac ggc ctc gac tgc<br>Pro Ala Ala Leu Arg Asp Leu Phe Arg Phe Ala Asp Gly Leu Asp Cys<br>                        125                    130                  135 | 498 |
| gcg ctc atg ctc atc ggc acc ctc ggc gcg ctc gtc cac ggg tgc tcg<br>Ala Leu Met Leu Ile Gly Thr Leu Gly Ala Leu Val His Gly Cys Ser<br>            140                    145                    150 | 546 |
| ctc ccc gtc ttc ctc cgc ttc ttc gcc gac ctc gtc gac tcc ttc ggc<br>Leu Pro Val Phe Leu Arg Phe Phe Ala Asp Leu Val Asp Ser Phe Gly<br>155                160                    165 | 594 |
| tcc cac gcc gac gac ccg gac acc atg gtc cgc ctc gtc gtc aag tac<br>Ser His Ala Asp Asp Pro Asp Thr Met Val Arg Leu Val Val Lys Tyr<br>    170                    175                  180 | 642 |
| gcc ttc tac ttc ctc gtc gtc gga gcg gca atc tgg gca tcc tcg tgg<br>Ala Phe Tyr Phe Leu Val Val Gly Ala Ala Ile Trp Ala Ser Ser Trp<br>185                190                    195                  200 | 690 |
| gca gag atc tct tgc tgg atg tgg acc ggc gag cgg cag tcg acg cgg<br>Ala Glu Ile Ser Cys Trp Met Trp Thr Gly Glu Arg Gln Ser Thr Arg<br>                    205                    210                  215 | 738 |
| atg cgg att cgg tac ctg gac gcg gcg ctg cgg cag gac gtg tcc ttc<br>Met Arg Ile Arg Tyr Leu Asp Ala Ala Leu Arg Gln Asp Val Ser Phe<br>        220                    225                  230 | 786 |
| ttc gac acc gac gtg cgg gcc tcg gac gtg atc tac gcc atc aac gcg<br>Phe Asp Thr Asp Val Arg Ala Ser Asp Val Ile Tyr Ala Ile Asn Ala<br>235                240                    245 | 834 |
| gac gcc gtg gtg gtg caa gga cgc cat cag cca gaa act ggg caa cct<br>Asp Ala Val Val Val Gln Gly Arg His Gln Pro Glu Thr Gly Gln Pro<br>    250                    255                  260 | 882 |
| cat cca cta cat ggc cac ctt cgt ggc cgg ctt cgt cgt ggg gtt cac<br>His Pro Leu His Gly His Leu Arg Gly Arg Leu Arg Arg Gly Val His<br>265                270                    275                  280 | 930 |
| ggc cgc gtg gca gct ggc gct ggt cac gct ggc cgt ggt gcc gct cat<br>Gly Arg Val Ala Ala Gly Ala Gly His Ala Gly Arg Gly Ala Ala His<br>                    285                    290                  295 | 978 |
| cgc cgt cat cgg cgg gct gag cgc cgc cgc gct cgc caa gct ctc gtc<br>Arg Arg His Arg Arg Ala Glu Arg Arg Arg Ala Arg Gln Ala Leu Val<br>        300                    305                  310 | 1026 |
| ccg cag cca gga cgc gct ctc ggg cgc cag cgg cat cgc gga gca ggc<br>Pro Gln Pro Gly Arg Ala Leu Gly Arg Gln Arg His Arg Gly Ala Gly<br>315                320                    325 | 1074 |
| gct cgc gca gat acg gat cgt gca ggc gtt cgt tgg cga gga gcg cga<br>Ala Arg Ala Asp Thr Asp Arg Ala Gly Val Arg Trp Arg Gly Ala Arg<br>    330                    335                  340 | 1122 |
| gat gcg ggc cta ctc ggc ggc gct ggc cgt ggc gca gag gat cgg cta<br>Asp Ala Gly Leu Leu Gly Gly Ala Gly Arg Gly Ala Glu Asp Arg Leu<br>345                350                    355                  360 | 1170 |
| ccg cag cgg ctt cgc caa ggg gct cgg cct cgg cgg cac cta ctt cac<br>Pro Gln Arg Leu Arg Gln Gly Ala Arg Pro Arg Arg His Leu Leu His<br>                    365                    370                  375 | 1218 |
| cgt ctt ctg ctg cta cgg gct cct gct ctg gta cgg cgg cca cct cgt<br>Arg Leu Leu Leu Leu Arg Ala Pro Ala Leu Val Arg Arg Pro Pro Arg<br>        380                    385                  390 | 1266 |
| gcg cgc cca gca cac caa cgg cgg gct cgc cat cgc acc atg ttc tcc<br>Ala Arg Pro Ala His Gln Arg Arg Ala Arg His Arg Thr Met Phe Ser<br>395                400                    405 | 1314 |
| gtc atg atc ggc gga ggc cct cgg cag tcg gcg ccg agc atg gcc gcg<br>Val Met Ile Gly Gly Gly Pro Arg Gln Ser Ala Pro Ser Met Ala Ala | 1362 |

```
            410                 415                 420
ttc gcc aag gcg cgt gtg gcg gct gcc aag atc ttc cgc atc atc gac     1410
Phe Ala Lys Ala Arg Val Ala Ala Lys Ile Phe Arg Ile Ile Asp
425                 430                 435                 440 cac agg ccg ggc atc tcc tcg cgc gac ggc gcg gag cca gag tcg gtg     1458
His Arg Pro Gly Ile Ser Ser Arg Asp Gly Ala Glu Pro Glu Ser Val
                445                 450                 455 acg ggg cgg gtg gag atg cgg ggc gtg gac ttc gcg tac ccg tcg cgg     1506
Thr Gly Arg Val Glu Met Arg Gly Val Asp Phe Ala Tyr Pro Ser Arg
        460                 465                 470 ccg gac gtc ccc atc ctg cgc ggc ttc tcg ctg agc gtg ccc gcc ggg     1554
Pro Asp Val Pro Ile Leu Arg Gly Phe Ser Leu Ser Val Pro Ala Gly
    475                 480                 485 aag acc atc gcg ctg gtg ggc agc tcc ggc tcc ggg aag agc acg gtg     1602
Lys Thr Ile Ala Leu Val Gly Ser Ser Gly Ser Gly Lys Ser Thr Val
490                 495                 500 gtg tcg ctc atc gag aga ttc tac gac ccc agc gca ggg caa atc ctg     1650
Val Ser Leu Ile Glu Arg Phe Tyr Asp Pro Ser Ala Gly Gln Ile Leu
505                 510                 515                 520 ctg gac ggg cac gac ctc agg tcg ctg gag ctg cgg tgg ctg cgg cgg     1698
Leu Asp Gly His Asp Leu Arg Ser Leu Glu Leu Arg Trp Leu Arg Arg
                525                 530                 535 cag atc ggg ctg gtg agc cag gag ccg gcg ctg ttc gcg acg agc atc     1746
Gln Ile Gly Leu Val Ser Gln Glu Pro Ala Leu Phe Ala Thr Ser Ile
        540                 545                 550 agg gag aac ctg ctg ctg ggg cgg gac agc cag agc gcg acg ctg gcg     1794
Arg Glu Asn Leu Leu Leu Gly Arg Asp Ser Gln Ser Ala Thr Leu Ala
    555                 560                 565 gag atg gag gag gcg gcc agg gtg gcc aac gcc cac tcc ttc atc atc     1842
Glu Met Glu Glu Ala Ala Arg Val Ala Asn Ala His Ser Phe Ile Ile
570                 575                 580 aaa ctc ccc gac ggc tac gac acg cag gtt ggg gag cgc ggc ctg cag     1890
Lys Leu Pro Asp Gly Tyr Asp Thr Gln Val Gly Glu Arg Gly Leu Gln
585                 590                 595                 600 ctc tcc ggt ggg cag aag cag cgc atc gcc atc gcc cgc gcc atg ctc     1938
Leu Ser Gly Gly Gln Lys Gln Arg Ile Ala Ile Ala Arg Ala Met Leu
                605                 610                 615 aag aac ccc gcc atc ctg ctg ctg gac gag gcc acc agc gcg ctg gac     1986
Lys Asn Pro Ala Ile Leu Leu Leu Asp Glu Ala Thr Ser Ala Leu Asp
        620                 625                 630 tcc gag tct gag aag ctc gtg cag gag gcg ctg gac cgc ttc atg atg     2034
Ser Glu Ser Glu Lys Leu Val Gln Glu Ala Leu Asp Arg Phe Met Met
    635                 640                 645 ggg cgc acc acc ctt ggt gat cgc gca aca ggc tgt cca cca tcc gca     2082
Gly Arg Thr Thr Leu Gly Asp Arg Ala Thr Gly Cys Pro Pro Ser Ala
650                 655                 660 aag gcc gac gtg gtg gcc gtg ctg cag ggc ggc gcc gtc tcc gag atg     2130
Lys Ala Asp Val Val Ala Val Leu Gln Gly Gly Ala Val Ser Glu Met
665                 670                 675                 680 agc gcg cac gac gag ctg atg gcc aag ggc gag aac ggc acc tac gcc     2178
Ser Ala His Asp Glu Leu Met Ala Lys Gly Glu Asn Gly Thr Tyr Ala
                685                 690                 695 aag ctc atc cgc atg cag gag cag gcg cac gag gcg gcg ctc gtc aac     2226
Lys Leu Ile Arg Met Gln Glu Gln Ala His Glu Ala Ala Leu Val Asn
        700                 705                 710 gcc cgc cgc agc agc gcc agg ccc tcc agc gcc cgc aac tcc gtc agc     2274
Ala Arg Arg Ser Ser Ala Arg Pro Ser Ser Ala Arg Asn Ser Val Ser
    715                 720                 725 tcg ccc atc atg acg cgc aac tcc tcc tac ggc cgc tcc ccc tac tcc     2322
```

```
                Ser Pro Ile Met Thr Arg Asn Ser Ser Tyr Gly Arg Ser Pro Tyr Ser
                    730                 735                 740 cgc cgc ctc tcc gac ttc tcc acc tcc gac ttc acc ctc tcc atc cac                    2370
Arg Arg Leu Ser Asp Phe Ser Thr Ser Asp Phe Thr Leu Ser Ile His
745                 750                 755                 760 gac ccg cac cac cac cac cgg acc atg gcg gac aag cag ctg gcg ttc                    2418
Asp Pro His His His His Arg Thr Met Ala Asp Lys Gln Leu Ala Phe
                765                 770                 775 cgc gcc ggc gcc agc tcc ttc ctg cgc ctc gcc agg atg aac tcg ccc                    2466
Arg Ala Gly Ala Ser Ser Phe Leu Arg Leu Ala Arg Met Asn Ser Pro
            780                 785                 790 gag tgg gcc tac gcg ctc gcc ggc tcc atc ggc tcc atg gtc tgc ggc                    2514
Glu Trp Ala Tyr Ala Leu Ala Gly Ser Ile Gly Ser Met Val Cys Gly
        795                 800                 805 tcc ttc agc gcc atc ttc gcc tac atc ctc agc gcc gtg ctc agc gtc                    2562
Ser Phe Ser Ala Ile Phe Ala Tyr Ile Leu Ser Ala Val Leu Ser Val
    810                 815                 820 tac tac gcg ccg gac ccg cgg tac atg aag cgc gag atc gca aaa tac                    2610
Tyr Tyr Ala Pro Asp Pro Arg Tyr Met Lys Arg Glu Ile Ala Lys Tyr
825                 830                 835                 840 tgt tac ctg ctc atc ggc atg tcc tcc gcg gcg ctg ctg ttc aac acg                    2658
Cys Tyr Leu Leu Ile Gly Met Ser Ser Ala Ala Leu Leu Phe Asn Thr
                845                 850                 855 gtg cag cac gtg ttc tgg gac acg gtg ggc gag aac ttg acc aag cgg                    2706
Val Gln His Val Phe Trp Asp Thr Val Gly Glu Asn Leu Thr Lys Arg
                860                 865                 870 gtg cgc gag aag atg ttc gcc gcc gtg ttc cgc aac gag atc gcc tgg                    2754
Val Arg Glu Lys Met Phe Ala Ala Val Phe Arg Asn Glu Ile Ala Trp
            875                 880                 885 ttc gac gcg gac gag aac gcc agc gcg cgc gtg acc gcc agg cta gcg                    2802
Phe Asp Ala Asp Glu Asn Ala Ser Ala Arg Val Thr Ala Arg Leu Ala
        890                 895                 900 ctg gac gcc cag aac gtg cgc tcc gcc atc ggg gac cgc atc tcc gtc                    2850
Leu Asp Ala Gln Asn Val Arg Ser Ala Ile Gly Asp Arg Ile Ser Val
905                 910                 915                 920 atc gtc cag aac tcg gcg ctg atg ctg gtg gcc tgc acc gcg ggg ttc                    2898
Ile Val Gln Asn Ser Ala Leu Met Leu Val Ala Cys Thr Ala Gly Phe
                925                 930                 935 gtc ctc cag tgg cgc ctc gcg ctc gtg ctc ctc gcc gtg ttc ccg ctc                    2946
Val Leu Gln Trp Arg Leu Ala Leu Val Leu Leu Ala Val Phe Pro Leu
                940                 945                 950 gtc gtg ggc gcc acc gtg ctg cag aag atg ttc atg aag ggc ttc tcg                    2994
Val Val Gly Ala Thr Val Leu Gln Lys Met Phe Met Lys Gly Phe Ser
            955                 960                 965 ggg gac ctg gag gcc gcg cac gcc agg gcc acg cag atc gcg ggc gag                    3042
Gly Asp Leu Glu Ala Ala His Ala Arg Ala Thr Gln Ile Ala Gly Glu
        970                 975                 980 gcc gtg gcc aac ctg cgc acc gtg gcc gcg ttc aac gcg gag cgc aag                    3090
Ala Val Ala Asn Leu Arg Thr Val Ala Ala Phe Asn Ala Glu Arg Lys
985                 990                 995                 1000 atc acg ggg ctg ttc gag gcc aac ctg cgc ggc ccg ctc cgg cgc tgc                    3138
Ile Thr Gly Leu Phe Glu Ala Asn Leu Arg Gly Pro Leu Arg Arg Cys
                1005                1010                1015 ttc tgg aag ggg cag atc gcc ggc agc ggc tac ggc gtg gcg cag ttc                    3186
Phe Trp Lys Gly Gln Ile Ala Gly Ser Gly Tyr Gly Val Ala Gln Phe
                1020                1025                1030 ctg ctg tac gcg tcc tac gcg ctg ggg ctg tgg tac gcg gcg tgg ctg                    3234
Leu Leu Tyr Ala Ser Tyr Ala Leu Gly Leu Trp Tyr Ala Ala Trp Leu
            1035                1040                1045
```

-continued

| | |
|---|---|
| gtg aag cac ggc gtg tcc gac ttc tcg cgc acc atc cgc gtg ttc atg<br>Val Lys His Gly Val Ser Asp Phe Ser Arg Thr Ile Arg Val Phe Met<br>1050                        1055                       1060 | 3282 |
| gtg ctg atg gtg tcc gcg aac ggc gcc gcc gag acg ctg acg ctg gcg<br>Val Leu Met Val Ser Ala Asn Gly Ala Ala Glu Thr Leu Thr Leu Ala<br>1065                        1070                       1075                       1080 | 3330 |
| ccg gac ttc atc aaa ggc ggg cgc gcg atg cgg tcg gtg ttc gag aca<br>Pro Asp Phe Ile Lys Gly Gly Arg Ala Met Arg Ser Val Phe Glu Thr<br>1085                        1090                       1095 | 3378 |
| atc gac cgc aag acg gag gtg gag ccc cac gac gtg gac gcg gcg ccg<br>Ile Asp Arg Lys Thr Glu Val Glu Pro His Asp Val Asp Ala Ala Pro<br>1100                        1105                       1110 | 3426 |
| gtg ccg gac ggc cca ggg gcg aag gtg gaa ctt aag cac gtg gac ttt<br>Val Pro Asp Gly Pro Gly Ala Lys Val Glu Leu Lys His Val Asp Phe<br>1115                        1120                       1125 | 3474 |
| ttg tac ccg tcg cgg ccg gac atc caa gtg ttc cgc gac ctg agc ctc<br>Leu Tyr Pro Ser Arg Pro Asp Ile Gln Val Phe Arg Asp Leu Ser Leu<br>1130                        1135                       1140 | 3522 |
| cgt gcg cgc gcc gga aaa acg ttg gcg ctg gtg ggg ccg agc ggg tcc<br>Arg Ala Arg Ala Gly Lys Thr Leu Ala Leu Val Gly Pro Ser Gly Ser<br>1145                        1150                       1155                       1160 | 3570 |
| ggc aag agc tcg gtc ctg gct ctg gtg cag cgg ttc tac aag ccc acg<br>Gly Lys Ser Ser Val Leu Ala Leu Val Gln Arg Phe Tyr Lys Pro Thr<br>                       1165                       1170                       1175 | 3618 |
| tcc ggg cgc gtg ctc ttg gac ggc aag gac gtg cgc aag tac aac ctg<br>Ser Gly Arg Val Leu Leu Asp Gly Lys Asp Val Arg Lys Tyr Asn Leu<br>                       1180                       1185                       1190 | 3666 |
| cgg gcg ctg cgg cgc gtg gtg gcg gtg gta ccg cag gag ccg ttc ctg<br>Arg Ala Leu Arg Arg Val Val Ala Val Val Pro Gln Glu Pro Phe Leu<br>1195                        1200                       1205 | 3714 |
| ttc gcg gcg agc atc cac gag aac atc gcg tac ggg cgc gag ggc gcg<br>Phe Ala Ala Ser Ile His Glu Asn Ile Ala Tyr Gly Arg Glu Gly Ala<br>1210                        1215                       1220 | 3762 |
| acg gag gcg gag gtg gtg gag gcg gcg gcg cag gcg aac gcg cac cgg<br>Thr Glu Ala Glu Val Val Glu Ala Ala Ala Gln Ala Asn Ala His Arg<br>1225                        1230                       1235                       1240 | 3810 |
| ttc atc gcg gcg ctg ccg gag ggg tac cgg acg cag gtg ggc gag cgc<br>Phe Ile Ala Ala Leu Pro Glu Gly Tyr Arg Thr Gln Val Gly Glu Arg<br>                       1245                       1250                       1255 | 3858 |
| ggg gtg cag ctg tcg ggg ggg cag cgg cag cgg atc gcg atc gcg cgc<br>Gly Val Gln Leu Ser Gly Gly Gln Arg Gln Arg Ile Ala Ile Ala Arg<br>                       1260                       1265                       1270 | 3906 |
| gcg ctg gtg aag cag gcg gcc atc gtg ctg ctg gac gag gcg acc agc<br>Ala Leu Val Lys Gln Ala Ala Ile Val Leu Leu Asp Glu Ala Thr Ser<br>1275                        1280                       1285 | 3954 |
| gcg ctg gac gcc gag tcg gag cgg tgc gtg cag gag gcg ctg gag cgc<br>Ala Leu Asp Ala Glu Ser Glu Arg Cys Val Gln Glu Ala Leu Glu Arg<br>1290                        1295                       1300 | 4002 |
| gcg ggg tcc ggg cgc acc acc atc gtg gtg gcg cac cgg ctg gcc acg<br>Ala Gly Ser Gly Arg Thr Thr Ile Val Val Ala His Arg Leu Ala Thr<br>1305                        1310                       1315                       1320 | 4050 |
| gtg cgc ggc gcg cac acc atc gcg gtc atc gac gac ggc aag gtg gcg<br>Val Arg Gly Ala His Thr Ile Ala Val Ile Asp Asp Gly Lys Val Ala<br>                       1325                       1330                       1335 | 4098 |
| gag cag ggg tcg cac tcg cac ctg ctc aag cac cat ccc gac ggg tgc<br>Glu Gln Gly Ser His Ser His Leu Leu Lys His His Pro Asp Gly Cys<br>                       1340                       1345                       1350 | 4146 |
| tac gcg cgg atg ctg cag ctt gca gcg gct gac ggg cgc ggc ggc cgg<br>Tyr Ala Arg Met Leu Gln Leu Ala Ala Ala Asp Gly Arg Gly Gly Arg<br>1355                        1360                       1365 | 4194 |

-continued

```
gcc cgg gcc gtc gtc ctc gtg caa cgg ggc cgc gta gga cgg aat gga    4242
Ala Arg Ala Val Val Leu Val Gln Arg Gly Arg Val Gly Arg Asn Gly
    1370                1375                1380 tgg atg gat ggg ttt ggt tcc tcg aga gat tgatgggtga ggaagctgaa       4292
Trp Met Asp Gly Phe Gly Ser Ser Arg Asp
1385                1390 gctccggatc aaatggtggt actccatgat cgcaacaatg aggggaaaaa aggaaaggag   4352
aaaatacggt ggttcatatg attgtacaat ttgacgatct gtttgagtcg gggttttagg   4412
atgatgtaaa ccttcactcg cctttttttt actcttgttt ctcatccgca tcagtatcat   4472
ctatctacat acagtgtcag agatgggaac tgatcccgca tcatcatcta cctcccaagg   4532
caccccagat tgtattaatg tacttagtta gcctgttta tatatactta taagtaccaa    4592
atagcagaat tttactcctt atctgcagta gcacgaaaga aaaaaaaaa aaaaaaaaa     4652 a                                                                    4653
```

<210> SEQ ID NO 3
<211> LENGTH: 1394
<212> TYPE: PRT
<213> ORGANISM: Zea mays

<400> SEQUENCE: 3

```
Met Ser Ser Ser Asp Pro Glu Glu Ile Arg Ala Arg Val Val Leu
 1               5                  10                  15

Gly Ser Pro His Ala Asp Gly Gly Asp Glu Trp Ala Arg Pro Glu Leu
                20                  25                  30

Glu Ala Phe His Leu Pro Ser Pro Ala His Gln Pro Pro Gly Phe Leu
            35                  40                  45

Ala Gly Gln Pro Glu Ala Ala Glu Gln Pro Thr Leu Pro Ala Pro Ala
        50                  55                  60

Gly Arg Ser Ser Ser Ser Asn Thr Pro Thr Thr Ser Ala Gly Gly
 65                  70                  75                  80

Gly Ala Ala Pro Pro Pro Ser Ser Pro Pro Pro Pro Ala Ser
                85                  90                  95

Leu Glu Thr Glu Gln Pro Pro Asn Ala Arg Pro Ala Ser Ala Gly Ala
                100                 105                 110

Asn Asp Ser Lys Lys Pro Thr Pro Pro Ala Ala Leu Arg Asp Leu Phe
            115                 120                 125

Arg Phe Ala Asp Gly Leu Asp Cys Ala Leu Met Leu Ile Gly Thr Leu
        130                 135                 140

Gly Ala Leu Val His Gly Cys Ser Leu Pro Val Phe Leu Arg Phe Phe
145                 150                 155                 160

Ala Asp Leu Val Asp Ser Phe Gly Ser His Ala Asp Pro Asp Thr
                165                 170                 175

Met Val Arg Leu Val Val Lys Tyr Ala Phe Tyr Phe Leu Val Val Gly
                180                 185                 190

Ala Ala Ile Trp Ala Ser Ser Trp Ala Glu Ile Ser Cys Trp Met Trp
            195                 200                 205

Thr Gly Glu Arg Gln Ser Thr Arg Met Arg Ile Arg Tyr Leu Asp Ala
        210                 215                 220

Ala Leu Arg Gln Asp Val Ser Phe Phe Asp Thr Asp Val Arg Ala Ser
225                 230                 235                 240

Asp Val Ile Tyr Ala Ile Asn Ala Asp Ala Val Val Val Gln Gly Arg
                245                 250                 255
```

-continued

His Gln Pro Glu Thr Gly Gln Pro His Pro Leu His Gly His Leu Arg
        260                 265                 270

Gly Arg Leu Arg Arg Gly Val His Gly Arg Val Ala Ala Gly Ala Gly
        275                 280                 285

His Ala Gly Arg Gly Ala Ala His Arg Arg His Arg Arg Ala Glu Arg
        290                 295                 300

Arg Arg Ala Arg Gln Ala Leu Val Pro Gln Pro Gly Arg Ala Leu Gly
305                 310                 315                 320

Arg Gln Arg His Arg Gly Ala Gly Ala Arg Ala Asp Thr Asp Arg Ala
                325                 330                 335

Gly Val Arg Trp Arg Gly Ala Arg Asp Ala Gly Leu Leu Gly Gly Ala
                340                 345                 350

Gly Arg Gly Ala Glu Asp Arg Leu Pro Gln Arg Leu Arg Gln Gly Ala
                355                 360                 365

Arg Pro Arg Arg His Leu Leu His Arg Leu Leu Leu Arg Ala Pro
        370                 375                 380

Ala Leu Val Arg Arg Pro Pro Arg Ala Arg Pro Ala His Gln Arg Arg
385                 390                 395                 400

Ala Arg His Arg Thr Met Phe Ser Val Met Ile Gly Gly Pro Arg
                405                 410                 415

Gln Ser Ala Pro Ser Met Ala Ala Phe Ala Lys Ala Arg Val Ala Ala
                420                 425                 430

Ala Lys Ile Phe Arg Ile Ile Asp His Arg Pro Gly Ile Ser Ser Arg
        435                 440                 445

Asp Gly Ala Glu Pro Glu Ser Val Thr Gly Arg Val Glu Met Arg Gly
        450                 455                 460

Val Asp Phe Ala Tyr Pro Ser Arg Pro Asp Val Pro Ile Leu Arg Gly
465                 470                 475                 480

Phe Ser Leu Ser Val Pro Ala Gly Lys Thr Ile Ala Leu Val Gly Ser
                485                 490                 495

Ser Gly Ser Gly Lys Ser Thr Val Val Ser Leu Ile Glu Arg Phe Tyr
        500                 505                 510

Asp Pro Ser Ala Gly Gln Ile Leu Leu Asp Gly His Asp Leu Arg Ser
        515                 520                 525

Leu Glu Leu Arg Trp Leu Arg Arg Gln Ile Gly Leu Val Ser Gln Glu
        530                 535                 540

Pro Ala Leu Phe Ala Thr Ser Ile Arg Glu Asn Leu Leu Gly Arg
545                 550                 555                 560

Asp Ser Gln Ser Ala Thr Leu Ala Glu Met Glu Ala Ala Arg Val
                565                 570                 575

Ala Asn Ala His Ser Phe Ile Ile Lys Leu Pro Asp Gly Tyr Asp Thr
                580                 585                 590

Gln Val Gly Glu Arg Gly Leu Gln Leu Ser Gly Gly Gln Lys Gln Arg
        595                 600                 605

Ile Ala Ile Ala Arg Ala Met Leu Lys Asn Pro Ala Ile Leu Leu Leu
        610                 615                 620

Asp Glu Ala Thr Ser Ala Leu Asp Ser Glu Ser Glu Lys Leu Val Gln
625                 630                 635                 640

Glu Ala Leu Asp Arg Phe Met Met Gly Arg Thr Thr Leu Gly Asp Arg
                645                 650                 655

Ala Thr Gly Cys Pro Pro Ser Ala Lys Ala Asp Val Val Ala Val Leu
                660                 665                 670

Gln Gly Gly Ala Val Ser Glu Met Ser Ala His Asp Glu Leu Met Ala

-continued

```
                675                 680                 685
Lys Gly Glu Asn Gly Thr Tyr Ala Lys Leu Ile Arg Met Gln Glu Gln
690                 695                 700
Ala His Glu Ala Ala Leu Val Asn Ala Arg Ser Ser Ala Arg Pro
705                 710                 715                 720
Ser Ser Ala Arg Asn Ser Val Ser Ser Pro Ile Met Thr Arg Asn Ser
                725                 730                 735
Ser Tyr Gly Arg Ser Pro Tyr Ser Arg Arg Leu Ser Asp Phe Ser Thr
            740                 745                 750
Ser Asp Phe Thr Leu Ser Ile His Asp Pro His His His Arg Thr
755                 760                 765
Met Ala Asp Lys Gln Leu Ala Phe Arg Ala Gly Ala Ser Ser Phe Leu
770                 775                 780
Arg Leu Ala Arg Met Asn Ser Pro Glu Trp Ala Tyr Ala Leu Ala Gly
785                 790                 795                 800
Ser Ile Gly Ser Met Val Cys Gly Ser Phe Ser Ala Ile Phe Ala Tyr
                805                 810                 815
Ile Leu Ser Ala Val Leu Ser Val Tyr Tyr Ala Pro Asp Pro Arg Tyr
            820                 825                 830
Met Lys Arg Glu Ile Ala Lys Tyr Cys Tyr Leu Leu Ile Gly Met Ser
            835                 840                 845
Ser Ala Ala Leu Leu Phe Asn Thr Val Gln His Val Phe Trp Asp Thr
850                 855                 860
Val Gly Glu Asn Leu Thr Lys Arg Val Arg Glu Lys Met Phe Ala Ala
865                 870                 875                 880
Val Phe Arg Asn Glu Ile Ala Trp Phe Asp Ala Asp Glu Asn Ala Ser
                885                 890                 895
Ala Arg Val Thr Ala Arg Leu Ala Leu Asp Ala Gln Asn Val Arg Ser
            900                 905                 910
Ala Ile Gly Asp Arg Ile Ser Val Ile Val Gln Asn Ser Ala Leu Met
            915                 920                 925
Leu Val Ala Cys Thr Ala Gly Phe Val Leu Gln Trp Arg Leu Ala Leu
930                 935                 940
Val Leu Leu Ala Val Phe Pro Leu Val Val Gly Ala Thr Val Leu Gln
945                 950                 955                 960
Lys Met Phe Met Lys Gly Phe Ser Gly Asp Leu Glu Ala Ala His Ala
                965                 970                 975
Arg Ala Thr Gln Ile Ala Gly Glu Ala Val Ala Asn Leu Arg Thr Val
            980                 985                 990
Ala Ala Phe Asn Ala Glu Arg Lys Ile Thr Gly Leu Phe Glu Ala Asn
            995                 1000                1005
Leu Arg Gly Pro Leu Arg Arg Cys Phe Trp Lys Gly Gln Ile Ala Gly
    1010                1015                1020
Ser Gly Tyr Gly Val Ala Gln Phe Leu Leu Tyr Ala Ser Tyr Ala Leu
1025                1030                1035                1040
Gly Leu Trp Tyr Ala Ala Trp Leu Val Lys His Gly Val Ser Asp Phe
                1045                1050                1055
Ser Arg Thr Ile Arg Val Phe Met Val Leu Met Val Ser Ala Asn Gly
            1060                1065                1070
Ala Ala Glu Thr Leu Thr Leu Ala Pro Asp Phe Ile Lys Gly Gly Arg
        1075                1080                1085
Ala Met Arg Ser Val Phe Glu Thr Ile Asp Arg Lys Thr Glu Val Glu
        1090                1095                1100
```

```
Pro His Asp Val Asp Ala Ala Pro Val Pro Asp Gly Pro Gly Ala Lys
1105                1110                1115                1120

Val Glu Leu Lys His Val Asp Phe Leu Tyr Pro Ser Arg Pro Asp Ile
            1125                1130                1135

Gln Val Phe Arg Asp Leu Ser Leu Arg Ala Arg Ala Gly Lys Thr Leu
        1140                1145                1150

Ala Leu Val Gly Pro Ser Gly Ser Gly Lys Ser Val Leu Ala Leu
    1155                1160                1165

Val Gln Arg Phe Tyr Lys Pro Thr Ser Gly Arg Val Leu Leu Asp Gly
    1170                1175                1180

Lys Asp Val Arg Lys Tyr Asn Leu Arg Ala Leu Arg Arg Val Val Ala
1185                1190                1195                1200

Val Val Pro Gln Glu Pro Phe Leu Phe Ala Ala Ser Ile His Glu Asn
            1205                1210                1215

Ile Ala Tyr Gly Arg Glu Gly Ala Thr Glu Ala Glu Val Val Glu Ala
        1220                1225                1230

Ala Ala Gln Ala Asn Ala His Arg Phe Ile Ala Ala Leu Pro Glu Gly
        1235                1240                1245

Tyr Arg Thr Gln Val Gly Glu Arg Gly Val Gln Leu Ser Gly Gly Gln
    1250                1255                1260

Arg Gln Arg Ile Ala Ile Ala Arg Ala Leu Val Lys Gln Ala Ala Ile
1265                1270                1275                1280

Val Leu Leu Asp Glu Ala Thr Ser Ala Leu Asp Ala Glu Ser Glu Arg
            1285                1290                1295

Cys Val Gln Glu Ala Leu Glu Arg Ala Gly Ser Gly Arg Thr Thr Ile
        1300                1305                1310

Val Val Ala His Arg Leu Ala Thr Val Arg Gly Ala His Thr Ile Ala
        1315                1320                1325

Val Ile Asp Asp Gly Lys Val Ala Glu Gln Gly Ser His Ser His Leu
    1330                1335                1340

Leu Lys His His Pro Asp Gly Cys Tyr Ala Arg Met Leu Gln Leu Ala
1345                1350                1355                1360

Ala Ala Asp Gly Arg Gly Gly Arg Ala Arg Ala Val Val Leu Val Gln
            1365                1370                1375

Arg Gly Arg Val Gly Arg Asn Gly Trp Met Asp Gly Phe Gly Ser Ser
        1380                1385                1390

Arg Asp
```